United States Patent [19]

Rhee et al.

[11] Patent Number: 5,800,541
[45] Date of Patent: Sep. 1, 1998

[54] COLLAGEN-SYNTHETIC POLYMER MATRICES PREPARED USING A MULTIPLE STEP REACTION

[75] Inventors: Woonza M. Rhee, Palo Alto; Richard A. Berg, Los Altos, both of Calif.

[73] Assignee: Collagen Corporation, Palo Alto, Calif.

[21] Appl. No.: 780,470

[22] Filed: Jan. 8, 1997

Related U.S. Application Data

[60] Continuation of Ser. No. 440,863, May 15, 1995, abandoned, which is a division of Ser. No. 236,769, May 2, 1994, Pat. No. 5,475,052, which is a continuation of Ser. No. 198,812, Feb. 18, 1994, abandoned, which is a continuation-in-part of Ser. No. 922,541, Jul. 30, 1992, Pat. No. 5,328,955, which is a continuation of Ser. No. 433,441, Nov. 14, 1989, Pat. No. 5,162,430, which is a continuation of Ser. No. 274,071, Nov. 21, 1988, abandoned.

[51] Int. Cl.$^6$ ............................ A61F 2/02; C08G 63/48
[52] U.S. Cl. ........................ 623/11; 623/11; 525/54.1; 523/113; 530/356; 424/422; 424/423
[58] Field of Search ................ 623/1, 11; 525/54.1, 525/54.2, 54.21–54.24, 937; 523/113, 115; 530/356, 840; 424/422, 423

[56] References Cited

U.S. PATENT DOCUMENTS

| | | | |
|---|---|---|---|
| 3,272,204 | 9/1966 | Artandi et al. | 606/151 |
| 3,949,073 | 4/1976 | Daniels et al. | 424/177 |
| 4,164,559 | 8/1979 | Miyata et al. | 424/14 |
| 4,179,337 | 12/1979 | Davis et al. | 434/181 |
| 4,488,911 | 12/1984 | Luck et al. | 106/161 |
| 4,557,764 | 12/1985 | Chu | 106/161 |
| 4,600,533 | 7/1986 | Chu | 530/356 |
| 4,642,117 | 2/1987 | Nguyen et al. | 623/11 |
| 4,655,980 | 4/1987 | Chu | 264/102 |
| 4,678,468 | 7/1987 | Hiroyoshi | 623/1 |
| 4,689,399 | 8/1987 | Chu | 530/356 |
| 4,725,671 | 2/1988 | Chu et al. | 530/356 |
| 4,980,403 | 12/1990 | Bateman et al. | 524/17 |
| 5,141,747 | 8/1992 | Scholz . | |
| 5,162,430 | 11/1992 | Rhee et al. | 525/54.1 |
| 5,292,802 | 3/1994 | Rhee et al. | 525/54.1 |

FOREIGN PATENT DOCUMENTS

| | | | |
|---|---|---|---|
| 4-227265 | 8/1992 | Japan | A61L 27/00 |
| WO 94/03155 | 2/1994 | WIPO | C08H 1/06 |

*Primary Examiner*—John G. Weiss
*Assistant Examiner*—Francis K. Cuddihy
*Attorney, Agent, or Firm*—Morrison & Foerster

[57] ABSTRACT

The present invention discloses collagen-synthetic polymer matrices which are prepared using a multiple step reaction. The first step of the reaction generally involves reacting collagen with a functionally activated synthetic hydrophilic polymer to form a collagen-synthetic polymer matrix. The synthetic hydrophilic polymer may be mono- or multifunctionally activated, but is preferably difunctionally activated, resulting in the formation of a crosslinked collagen matrix. The second step comprises modifying the collagen-synthetic polymer matrix according to one or more of the following methods: further crosslinking the matrix using a multifunctionally activated synthetic polymer, conjugating the matrix using a monofunctionally activated synthetic polymer, coupling biologically active molecules or glycosaminoglycans to the matrix, crosslinking the matrix using conventional chemical crosslinking agents, or modifying the collagen in the matrix by means of various chemical reactions. An optional third step may include further modification of the collagen-synthetic polymer matrix by covalently binding, for example, biologically active molecules or glycosaminoglycans to the matrix by means of available active groups on the synthetic hydrophilic polymers. Collagen-synthetic polymer matrices prepared according to the methods of the present invention have very low immunogenicity and can therefore be used to prepare biocompatible implants for use in a variety of medical applications.

55 Claims, 8 Drawing Sheets

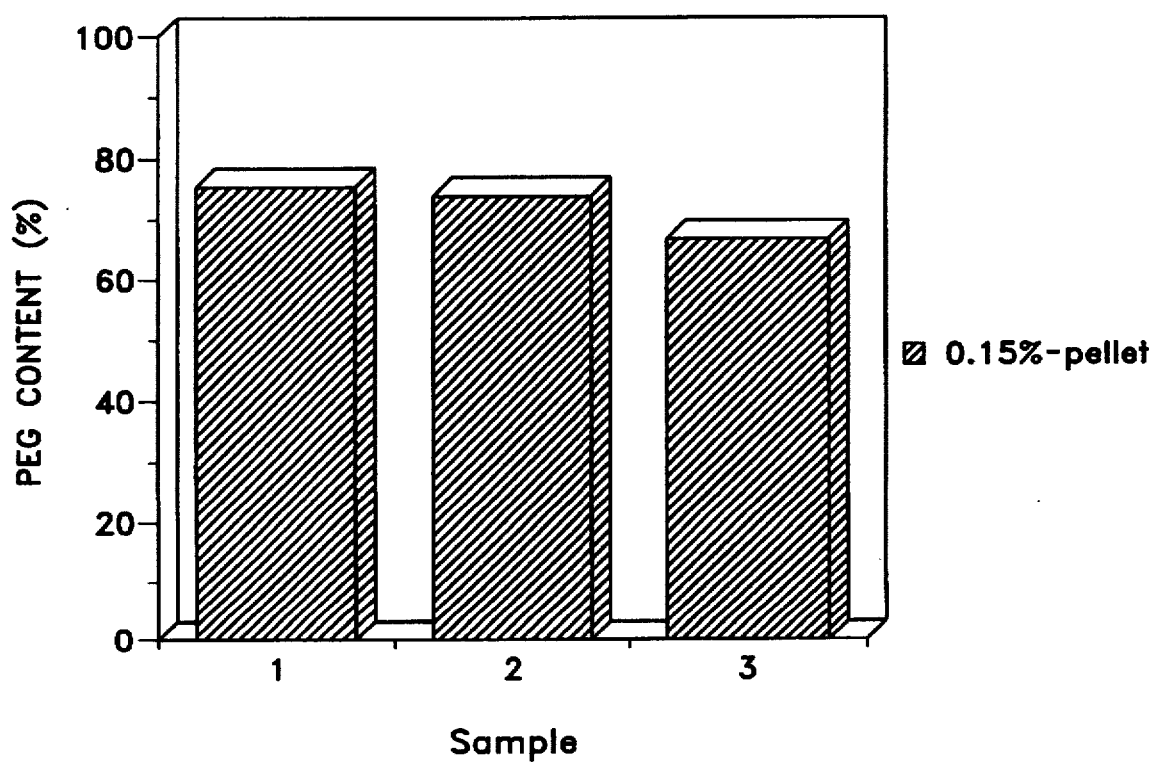
Figure 1: PEG Content in gel prepared from 0.15% w/v SPEG

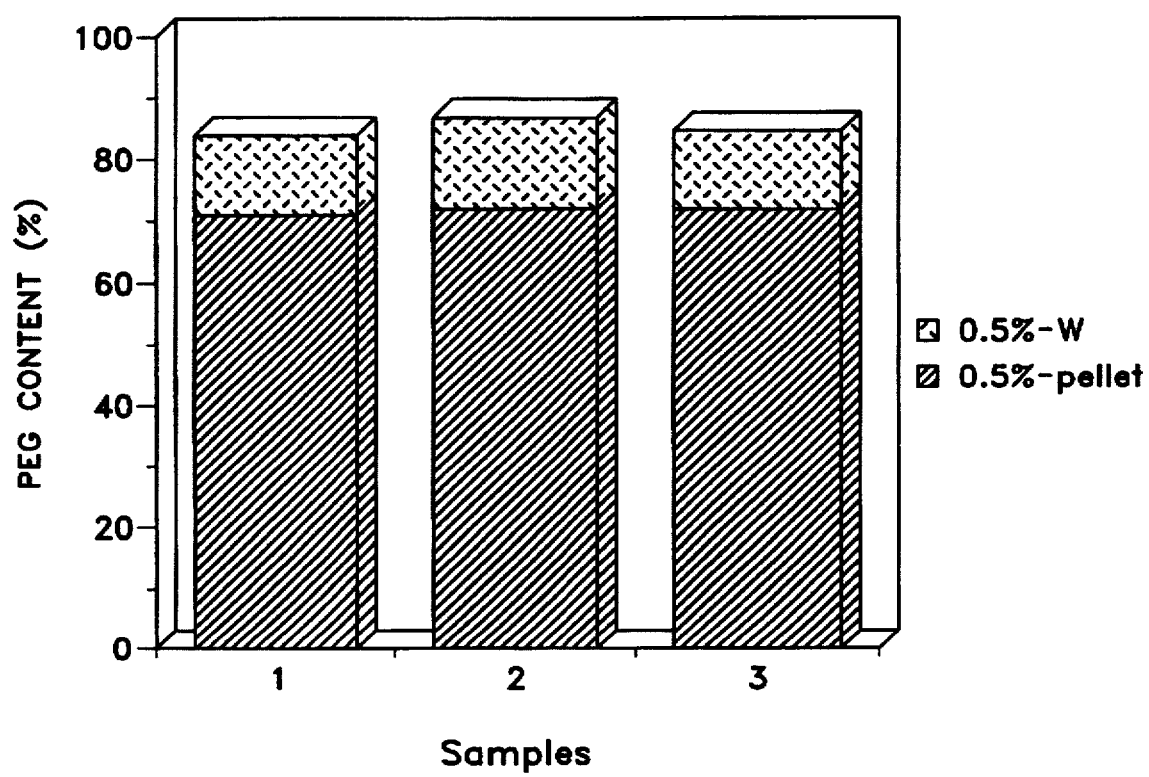

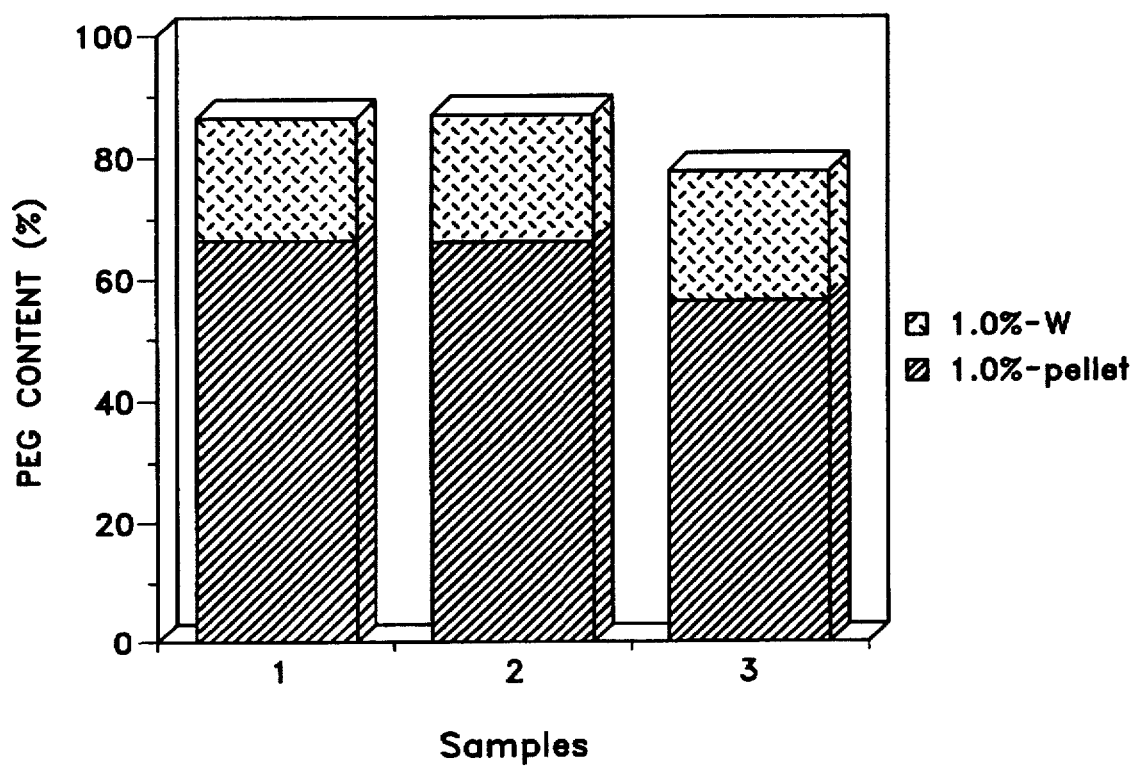
Figure 3: PEG Content in gel prepared from 1.0% w/v SPEG

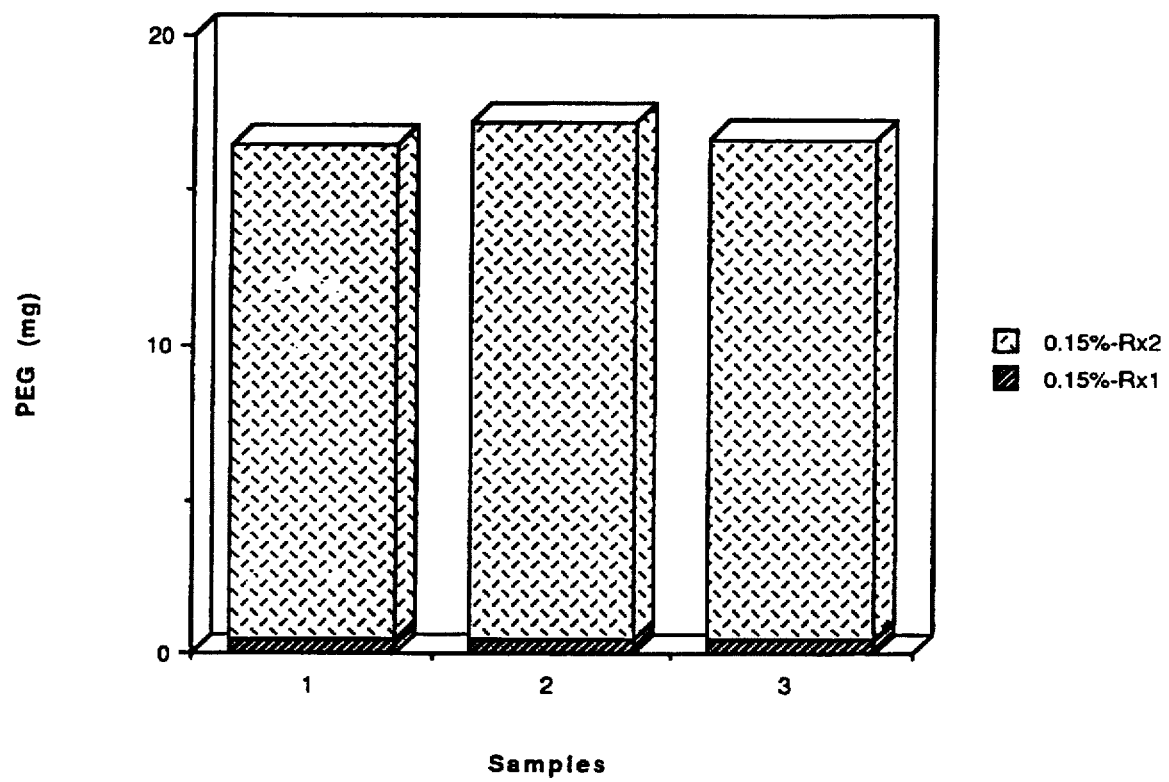

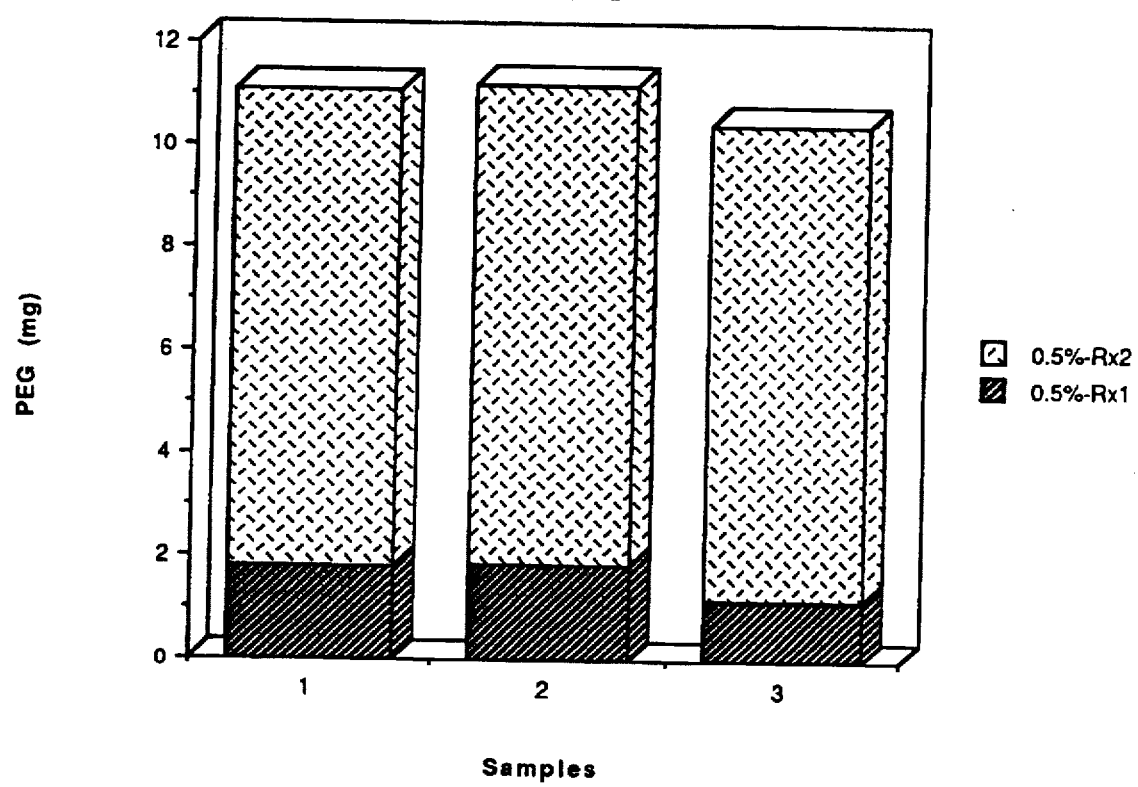

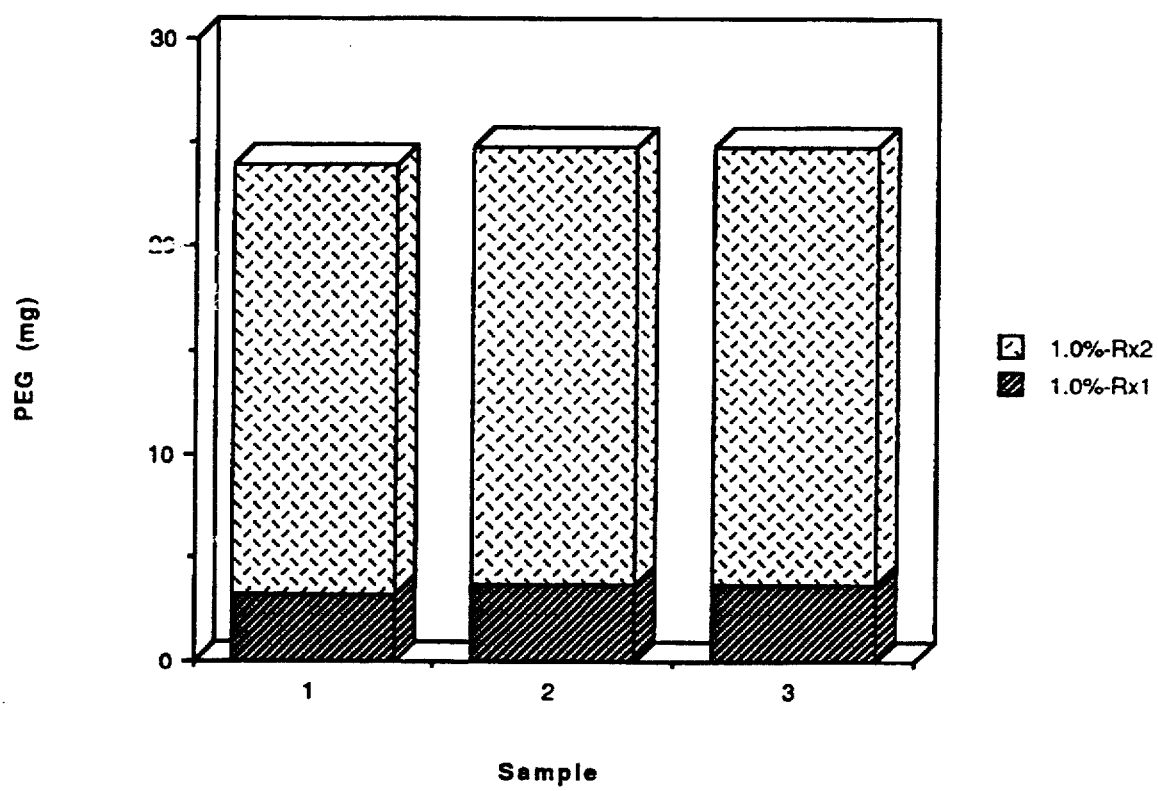

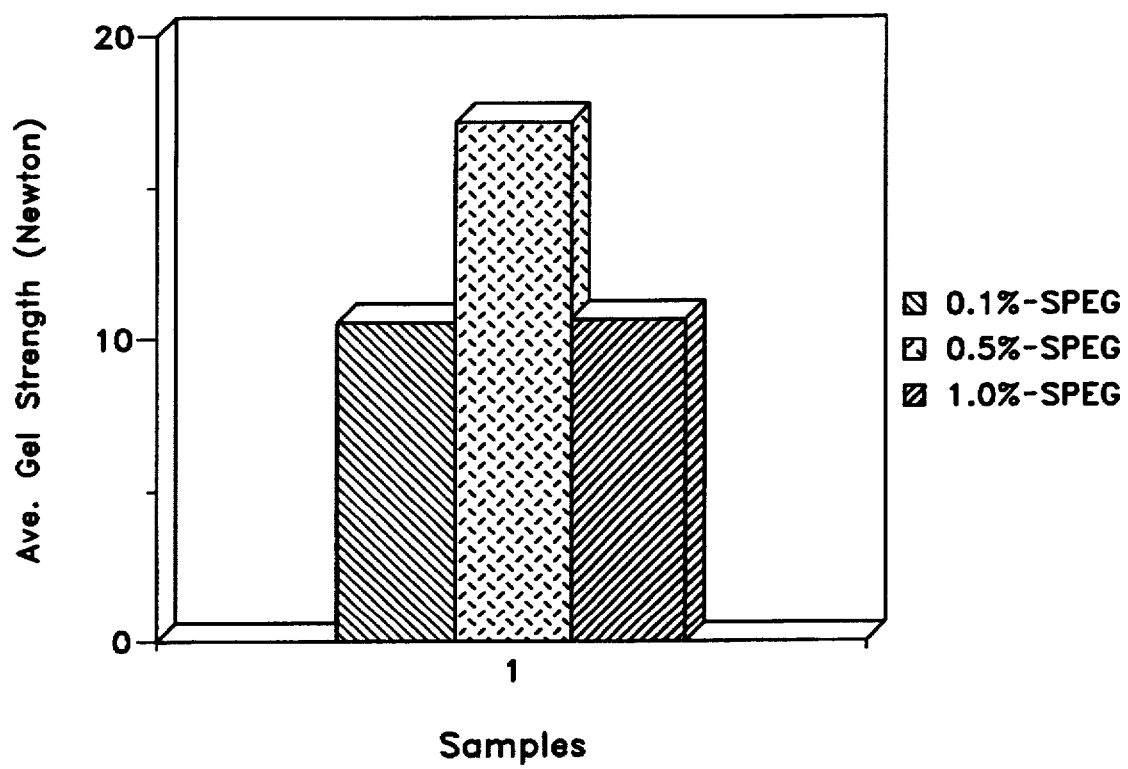

Figure 8: Coated Implant
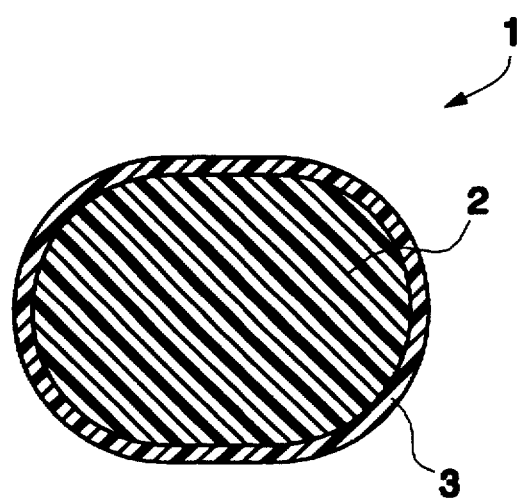

COLLAGEN-SYNTHETIC POLYMER MATRICES PREPARED USING A MULTIPLE STEP REACTION

CROSS-REFERENCES

This application is a continuation of U.S. application Ser. No. 08/440,863, filed May 15, 1995, now abandoned, which is a divisional of application Ser. No. 08/236,769, filed May 2, 1994, now U.S. Pat. No. 5,475,052 which issued on Dec. 12, 1995, which is a continuation of application Ser. No. 08/198,812, filed Feb. 18, 1994, now abandoned, which is a continuation-in-part of U.S. application Ser. No. 07/922,541, filed Jul. 30, 1992, now U.S. Pat. No. 5,328,955, which issued on Jul. 12, 1994, which is a continuation of U.S. application Ser. No. 07/433,441, filed Nov. 14, 1989, now U.S. Pat. No. 5,162,430, which issued on Nov. 10, 1992, which is a continuation of U.S. application Ser. No. 07/274,071, filed Nov. 21, 1988, now abandoned, which applications and issued patents are incorporated herein by reference in full, and to which currently pending applications we claim priority under 35 U.S.C. 120.

FIELD OF THE INVENTION

This invention relates to collagen-synthetic polymer matrices which are prepared using a multiple step reaction. The first step of the reaction generally comprises preparation of the collagen-synthetic polymer matrix by reacting collagen with a functionally activated synthetic hydrophilic polymer. Subsequent steps involve chemical modification of the collagen-synthetic polymer matrix by reacting the matrix with a variety of chemical substances, depending on the desired end use application. Such collagen-synthetic polymer matrices and the methods for preparing them are disclosed herein.

BACKGROUND OF THE INVENTION

Daniels et al., U.S. Pat. No. 3,949,073, disclosed the preparation of soluble collagen by dissolving tissue in aqueous acid, followed by enzymatic digestion. The resulting atelopeptide collagen is soluble, and substantially less immunogenic than unmodified collagen. It may be injected into suitable locations of a subject with a fibril-formation promoter (described as a polymerization promoter in the patent) to form fibrous collagen implants in situ, for augmenting hard or soft tissue. This material is now commercially available from Collagen Corporation (Palo Alto, Calif.) under the trademark Zyderm® Collagen Implant.

Miyata et al., U.S. Pat. No. 4,164,559, disclosed an ophthalmic drug delivery system comprising a chemically modified collagen thin membrane carrier.

Davis et al., U.S. Pat. No. 4,179,337, disclosed a physiologically active, water-soluble polypeptide composition comprising a physiologically active polypeptide coupled with a coupling agent to polyethylene glycol or polypropylene glycol.

Luck et al., U.S. Pat. No. 4,488,911, disclosed a method for preparing collagen in solution (CIS), wherein native collagen is extracted from animal tissue in dilute aqueous acid, followed by digestion with an enzyme such as pepsin, trypsin, or Pronase® (a trademark of American Hoechst Corporation, Somerville, N.J.). The enzymatic digestion removes the telopeptide portions of the collagen molecules, providing "atelopeptide" collagen in solution. The atelopeptide collagen in solution so produced is substantially nonimmunogenic, and is also substantially non-crosslinked due to loss of the primary crosslinking regions. The collagen in solution may then be precipitated by dialysis in a moderate shear environment to produce collagen fibers which resemble native collagen fibers. The precipitated, reconstituted fibers may additionally be crosslinked using a chemical agent (for example, aldehydes such as formaldehyde and glutaraldehyde), heat, or radiation. The resulting products are suitable for use in medical implants due to their biocompatibility and reduced immunogenicity.

Chu, U.S. Pat. No. 4,557,764, disclosed a "second nucleation" collagen precipitate which exhibits a desirable malleability and putty-like consistency. Collagen is provided in solution (e.g., at 2–4 mg/ml), and a "first nucleation product" is precipitated by rapid titration and centrifugation. The remaining supernatant (containing the bulk of the original collagen) is then decanted and allowed to stand overnight. The precipitated second nucleation product is collected by centrifugation.

Chu, U.S. Pat. Nos. 4,600,533; 4,655,980; 4,689,399; and 4,725,617, disclosed methods for preparing collagen membranes having high tensile strength by compressing and drying collagen gels.

Nguyen et al., U.S. Pat. No. 4,642,117, disclosed an injectable collagen material composed of reconstituted, mechanically sheared atelopeptide collagen fibers, which are prepared by passing reconstituted collagen fibers repeatedly through a rigid mesh screen, until a substantial reduction in fiber size and size heterogeneity is achieved. The mechanically sheared fibers may be subsequently crosslinked.

Ramshaw et al., U.S. Pat. No. 4,980,403, disclosed the precipitation of bovine collagen (types I, II, and III) from aqueous PEG solutions, where there is no binding between collagen and PEG.

Miyata et al., Japanese patent application 4227265, published Aug. 17, 1992, discloses a composition comprising atelopeptide collagen linked to a polyepoxy compound. The composition is injected into the body to obtain sustained skin-lifting effects.

U.S. Pat. No. 5,162,430, issued Nov. 10, 1992 to Rhee et al., and commonly owned by the assignee of the present application, discloses collagen-synthetic polymer conjugates and methods of covalently binding collagen to synthetic hydrophilic polymers. This patent further disclosed binding biologically active agents to synthetic polymer molecules; then reacting with collagen to form a three-part collagen-synthetic polymer-active agent conjugate. Commonly owned, U.S. Pat. No. 5,292,802, issued Mar. 8, 1994, discloses methods for making tubes comprising collagen-synthetic polymer conjugates. Commonly owned, allowed U.S. application Ser. No. 07/922,541, filed Jul. 30, 1992, discloses various activated forms of polyethylene glycol and various linkages which can be used to produce collagen-synthetic polymer conjugates having a range of physical and chemical properties. Commonly owned, copending U.S. application Ser. No. 07/984,933, filed Dec. 2, 1992, discloses methods for coating implants with collagen-synthetic polymer conjugates.

Commonly owned, copending U.S. application Ser. No. 08/146,843, filed Nov. 3, 1993, discloses conjugates comprising various species of glycosaminoglycan covalently bound to synthetic hydrophilic polymers, which are optionally bound to collagen as well. Commonly owned, copending U.S. application Ser. No. 08/147,227, filed Nov. 3, 1993, discloses collagen-polymer conjugates comprising chemically modified collagens such as, for example, succinylated collagen or methylated collagen, covalently bound to synthetic hydrophilic polymers to produce optically clear materials for use in ophthalmic or other medical applications.

Commonly owned U.S. application Ser. No. 08/201,860, filed Feb. 17, 1994, discloses collagen-synthetic polymer conjugates prepared using collagens having controlled fiber size distributions, which can be obtained, for example, by manipulation of the pH of the collagen.

All publications cited above and herein are incorporated herein by reference to describe and disclose the subject matter for which it is cited.

We now disclose collagen-synthetic polymer conjugate compositions prepared using a multiple step reaction.

DEFINITIONS

It must be noted that, as used in this specification and the appended claims, the singular forms "a", "an", and "the" include plural referents unless the context clearly dictates otherwise. For example, reference to "a conjugate" includes one or more conjugate molecules, reference to "an article" includes one or more different types of articles known to those skilled in the art and reference to "the collagen" includes mixtures of different types of collagens and so forth.

Specific terminology of particular importance to the description of the present invention is defined below:

The term "aqueous mixture" of collagen includes liquid solutions, suspensions, dispersions, colloids, and the like, containing collagen and water.

The term "atelopeptide collagen" refers to collagens which have been chemically treated or otherwise processed to remove the telopeptide regions, which are known to be responsible for causing an immune response in humans to collagens from other animal, such as bovine, sources.

The term "available lysine residue" as used herein refers to lysine side chains exposed on the outer surface of collagen molecules, which have primary amino groups capable of reacting with activated polymeric glycols. The number of available lysine residues may be determined by reaction with sodium 2,4,6-trinitrobenzenesulfonate (TNBS).

The term "biologically active molecules" is used to describe molecules such as growth factors, cytokines, and active peptides (which may be either naturally occurring or synthetic) which aid in the healing or regrowth of normal tissue. The function of biologically active molecules such as cytokines and growth factors is two-fold: 1) they can incite local cells to produce new tissue, or 2) they can attract cells to the site in need of correction. As such, biologically active molecules serve to encourage "biological anchoring" of an implant within the host tissue. Biologically active molecules useful in conjunction with the collagen-synthetic polymer conjugates of the present invention include, but are not limited to, cytokines such as interferons (IFN), tumor necrosis factors (TNF), interleukins, colony stimulating factors (CSFs), and growth factors such as osteogenic factor extract (OFE), epidermal growth factor (EGF), transforming growth factor (TGF) alpha, TGF-β (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, erythropoietin (EPO), and nerve growth factor (NGF). The term "biologically active molecules" as used herein is further intended to encompass drugs such as antibiotics, anti-inflammatories, antithrombotics, and the like.

The terms "chemically conjugated" and "conjugated" as used herein mean attached through a covalent chemical bond. In the practice of the invention, a hydrophilic synthetic polymer and a collagen molecule may be covalently conjugated directly to each other by means of a functionally active group on the synthetic hydrophilic polymer, or the collagen and synthetic polymer may be covalently conjugated using a linking radical so that the hydrophilic synthetic polymer and collagen are each bound to the radical, but not directly to each other. The term "collagen" as used herein refers to all forms of collagen which can be used as starting materials, including those-which have been recombinantly produced, extracted from naturally occurring sources (such as bovine corium or human placenta), processed, or otherwise modified.

The term "collagen-in-solution" or "CIS" refers to collagen in an acidic solution having a pH of approximately 3 or less, such that the collagen is in the nonfibrillar form.

The term "collagen suspension" refers to a suspension of collagen fibers in an aqueous carrier, such as water or phosphate-buffered saline (PBS).

The term "collagen-synthetic polymer" refers to collagen chemically conjugated to a synthetic hydrophilic polymer, within the meaning of this invention. For example, "PEG-collagen" denotes a composition of the invention wherein molecules of collagen are covalently conjugated to molecules of polyethylene glycol (PEG). "Crosslinked collagen" refers to a collagen composition in which collagen molecules are linked by covalent bonds with multifunctionally activated synthetic hydrophilic polymers, such as difunctionally activated polyethylene glycol.

The term "dehydrated" means that the material is air-dried or lyophilized to remove substantially all unbound water.

The term "difunctionally activated" refers to synthetic hydrophilic polymers which have been chemically derivatized so as to have two functional groups capable of reacting with available lysine residues on collagen molecules. The two functionally activate groups on a difunctionally activated synthetic hydrophilic polymer are generally located one at each end of the polymer chain. Each functionally activated group on a difunctionally activated synthetic hydrophilic polymer molecule is capable of covalently binding with a collagen molecule, thereby effecting crosslinking between the collagen molecules.

The term "effective amount" refers to the amount of a composition required in order to obtain the effect desired. Thus, a "tissue growth-promoting amount" of a composition containing a biologically active molecule refers to the amount of biologically active molecule needed in order to stimulate tissue growth to a detectable degree. Tissue, in this context, includes any tissue of the body. The actual amount which is determined to be an effective amount will vary depending on factors such as the size, condition, sex, and age of the patient, and can be more readily determined by the caregiver.

The term "fibrillar collagen" refers to collagens in which the triple helical molecules aggregate to form thick fibers due to intermolecular charge interactions, such that a composition containing fibrillar collagen will be more or less opaque.

The term "functionally activated" refers to synthetic hydrophilic polymers which have been chemically derivatized so as to have one or more functional group capable of reacting with available lysine residues on collagen molecules at various locations along the polymer chain.

The terms "implant" and "solid implant" refer to any semi-solid or solid object which is intended for insertion and long- or short-term use within the body.

The term "in situ" as used herein means at the site of administration.

The term "in situ crosslinking" as used herein refers to crosslinking of a collagen implant to a patient's own collagen using multifunctionally activated synthetic polymers, wherein one functionally activated end of the synthetic polymer is covalently conjugated to a collagen molecule in the collagen implant, and the other functionally activated end of the polymer is free to covalently bind to collagen molecules within the patient's own tissue.

The term "molecular weight" as used herein refers to the weight average molecular weight of a number of molecules in any given sample, as commonly used in the art. Thus, a sample of PEG 2000 might contain a statistical mixture of polymer molecules ranging in weight from, for example, 1500 to 2500, with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20,000.

The term "monofunctionally activated" refers to synthetic hydrophilic polymers which have been chemically derivatized so as to have one functional group capable of reacting with an available lysine residue on a collagen molecule. The functionally activate group on a monofunctionally activated synthetic hydrophilic polymer is generally located at one end of the polymer chain. Because they can only bind to one collagen molecule at a time, monofunctionally activated synthetic hydrophilic polymers are not capable of effecting crosslinking between collagen molecules.

The term "multifunctionally activated" refers to synthetic hydrophilic polymers which have been chemically derivatized so as to have two or more functional groups capable of reacting with available lysine residues on collagen molecules at various locations along the polymer chain. Each functionally activate group on a multifunctionally activated synthetic hydrophilic polymer molecule is capable of covalently binding with a collagen molecule, thereby effecting crosslinking between the collagen molecules. Types of multifunctionally activated hydrophilic synthetic polymers include difunctionally activated, tetrafunctionally activated, and star-branched polymers.

The term "multiple step reaction" as used herein refers to a specific series of reaction steps used to prepare, and subsequently modify, a matrix comprising collagen covalently bound to a hydrophilic synthetic polymer. Such multiple step reactions generally comprise at least two reaction steps, the first of which comprises covalently binding collagen to a synthetic hydrophilic polymer. Subsequent (second, third, fourth, etc.) reaction steps are directed to further modification of the collagen-synthetic polymer matrix. Such subsequent steps will vary according to, and are therefore determined by, the specific chemical and biological characteristics required for the desired end use application of the collagen-synthetic polymer matrix.

The term "nonfibrillar collagen" refers to collagens in which the triple helical molecules do not aggregate to form thick fibers, such that a composition containing nonfibrillar collagen will be optically clear.

The term "optically clear" as used herein refers to an article which transmits at least 90% of the visible light directed at it at a thickness of 1 mm.

The term "pharmaceutically acceptable fluid carrier" refers to fluid carriers for use in injectable or implantable formulations which are biocompatible (i.e., do not invoke an adverse response when injected or otherwise implanted within the human body) and which may be either aqueous, such as water or PBS, or nonaqueous, such as a biocompatible oil.

The term "sufficient amount" as used herein is applied to the amount of acid, base, or salt which must be added to the collagen composition in order to achieve the desired pH and/or fiber size.

The terms "synthetic hydrophilic polymer" or "synthetic polymer" refer to polymers which have been synthetically produced and which are hydrophilic, but not necessarily water-soluble. Examples of synthetic hydrophilic polymers which can be used in the practice of the present invention are polyethylene glycol (PEG), polyoxyethylene, polymethylene glycol, polytrimethylene glycols, polyvinylpyrrolidones, polyoxyethylene-polyoxypropylene block polymers and copolymers, and derivatives thereof. Naturally occurring polymers such as proteins, starch, cellulose, heparin, hyaluronic acid, and derivatives thereof are expressly excluded from the scope of this definition.

The terms "treat" and "treatment" as used herein refer to replacement, augmentation, repair, prevention, or alleviation of defects related to soft and/or hard tissue. Additionally, "treat" and "treatment" also refer to the prevention, maintenance, or alleviation of disorders or disease using a biologically active molecule coupled to or mixed with the conjugates of the invention.

Except as otherwise defined above, all technical and scientific terms used herein have the same meaning as commonly understood by one of ordinary skill in the art to which this invention belongs. Although any methods and materials similar or equivalent to those described herein may be useful in the practice or testing of the present invention, only the preferred methods and materials are described below. It is not intended that the invention be limited to these preferred embodiments, however. The invention is intended to have the scope defined by the attached claims.

SUMMARY OF THE INVENTION

The present invention discloses collagen-synthetic polymer matrices prepared by the process of reacting collagen with a first synthetic hydrophilic polymer to form a collagen-synthetic polymer matrix, then further reacting the collagen-synthetic polymer matrix with a chemical substance selected from the group consisting of a second synthetic hydrophilic polymer, a biologically active agent, a glycosaminoglycan or its derivatives, a chemical crosslinking agent, an esterifying agent, an amidating agent, an acylating agent, an amino acid, a peptide, or combinations thereof.

The invention additionally discloses in detail a preferred embodiment of the invention wherein the first step reaction of collagen with a first synthetic hydrophillic polymer to form a collagen-synthetic polymer matrix is followed by a second step comprising further reacting the collagen-synthetic polymer matrix with a second synthetic hydrophilic polymer.

Additionally disclosed are collagen-synthetic polymer matrices containing biologically active agents or glycosaminoglycans. Such matrices are prepared using a multiple step reaction, wherein the first step comprises reacting collagen with a first synthetic hydrophilic polymer to form a collagen-synthetic polymer matrix, a second step comprises further reacting the collagen-synthetic polymer matrix with a second synthetic hydrophilic polymer, and a third step comprises covalently binding the collagen-synthetic polymer matrix to a biologically active agent or a glycosaminoglycan or its derivatives.

The resulting compositions have low immunogenicity and, as such, can be used in a variety of medical applications, such as in drug delivery systems or in the preparation of various formed implants.

Further disclosed are the multiple step processes for preparing the collagen-synthetic polymer matrices described above.

One feature of the present invention is that collagen-synthetic polymer matrices can be prepared in a more controlled and reproducible manner using a specific sequence of reaction steps (i.e., a "multiple step reaction").

Another feature of the present invention is that the collagen-synthetic polymer matrices can be tailored specifically to have the physical and chemical characteristics desired for use in a variety of therapeutic applications, depending on the specific series of reaction steps employed.

Yet another feature of the present invention is that collagen-synthetic polymer matrices containing biologically active agents can be prepared in an efficient, more controlled manner, to provide a matrix which provides for maximum utilization of biologically active agents.

An important feature of the present invention is that the collagen-synthetic polymer matrices can be used to coat synthetic implants or prosthetic devices for the purpose of improving the biocompatibility of the implant or imparting biological activity to the implant, in the case where biologically active molecules are bound to the collagen-synthetic polymer matrix.

Another feature of the present invention is that implantable devices can be prepared such that biologically active agents are distributed along the surface of the implant, where they can exert their greatest therapeutic effect.

BRIEF DESCRIPTION OF THE DRAWINGS

FIG. 1 shows the relative amounts of unreacted PEG and bound PEG as a percentage of the total amount of PEG added to the collagen for PEG-collagen matrices having a PEG concentration of 1.5 mg S-PEG per ml collagen.

FIG. 2 shows the relative amounts of unreacted PEG and bound PEG as a percentage of the total amount of PEG added to the collagen for PEG-collagen matrices having a PEG concentration of 5.0 mg S-PEG per ml collagen.

FIG. 3 shows the relative amounts of unreacted PEG and bound PEG as a percentage of the total amount of PEG added to the collagen for PEG-collagen matrices having a PEG concentration of 10.0 mg S-PEG per ml collagen.

FIG. 4 shows the actual amount, in milligrams, of bound PEG found in PEG-collagen matrices prepared using a two-step reaction, compared to PEG-collagen matrices prepared using a single step reaction, for matrices having an original PEG concentration of 1.5 mg S-PEG per ml collagen.

FIG. 5 shows the actual amount, in milligrams, of bound PEG found in PEG-collagen matrices prepared using a two-step reaction, compared to PEG-collagen matrices prepared using a single step reaction, for matrices having an original PEG concentration of 5.0 mg S-PEG-per ml collagen.

FIG. 6 shows the actual amount, in milligrams, of bound PEG found in PEG-collagen matrices prepared using a two-step reaction, compared to PEG-collagen matrices prepared using a single step reaction, for matrices having an original PEG concentration of 10.0 mg S-PEG per ml collagen.

FIG. 7 shows gel strength in Newtons (measured using the Instron Model 4202) for PEG-collagen matrices having PEG concentrations of 1.5, 5.0, and 10.0 mg S-PEG per ml collagen.

FIG. 8 shows a coated implant.

DETAILED DESCRIPTION OF THE PREFERRED EMBODIMENTS OF THE INVENTION

Background of the Invention

In our earlier applications, we disclosed collagen-synthetic polymer conjugate compositions containing biologically active agents such as growth factors. Two methods of incorporating growth factors into the collagen-synthetic polymer conjugate compositions were disclosed in these applications: admixing the growth factors with the collagen-synthetic polymer conjugate, or covalently binding the growth factors to the collagen-synthetic polymer conjugate to form a three-part collagen-synthetic polymer-growth factor conjugate.

U.S. Pat. No. 5,162,430 disclosed two methods by which these three-part conjugates could be prepared. The first of these was by incorporating the factor into the collagen prior to treatment with an activated synthetic hydrophilic polymer. The second method comprised reacting the factor with a molar excess of a difunctionally activated synthetic hydrophilic polymer, then adding the conjugated factor to an aqueous collagen mixture and allowing it to react to form a collagen-synthetic polymer-growth factor conjugate.

We have since discovered that it is possible to first form a crosslinked collagen-synthetic polymer matrix by reacting collagen with an activated synthetic hydrophilic polymer, then further reacting the matrix with a variety of chemical substances, including biologically active agents such as growth factors, and also including, without limitation, additional synthetic hydrophilic polymers, glycosaminoglycans, other chemical crosslinking agents, esterifying agents, amidating agents, acylating agents, amino acids, or peptides. These chemical substances can be bound to the collagen-synthetic polymer matrix as a second step, after matrix formation, by means of either available amino groups on remaining lysine residues on the collagen in the matrix, or remaining unreacted functional groups on synthetic polymer molecules bound to the matrix. In a preferred embodiment, the collagen-synthetic polymer matrix is first formed by reacting collagen with a multifunctionally activated synthetic hydrophilic polymer, then the matrix is reacted with a second functionally activated synthetic polymer (which may be the same or different from the first polymer) to provide available functional groups to which additional chemical substituents, such as biologically active agents or glycosaminoglycans, can be tethered in a third-step reaction. The physical and chemical characteristics of the resulting collagen-synthetic polymer matrix will, of course, depend on the specific series of reactions and the types of reactants employed.

The processes of the present invention provide for the efficient production of collagen-synthetic polymer matrices having desired characteristics, such as biologically active molecules tethered to the surfaces of the matrix where they can exert their greatest biological effect. In accordance with a preferred method for preparing the collagen-synthetic polymer matrices of the present invention, (a) a functionally activated hydrophilic synthetic polymer is prepared or otherwise provided, (b) collagen is covalently bound to the synthetic hydrophilic polymer to provide a collagen-synthetic polymer matrix, (c) the collagen-synthetic polymer matrix is then modified by one or more of a variety of chemical reactions, and, optionally, (d) the modified collagen-polymer matrix is further alterered by covalently binding, for example, biologically active molecules or glycosaminoglycans to the matrix by means of available functional groups on the surface of the modified collagen-synthetic polymer matrix.

Activation of Synthetic Hydrophilic Polymers

A critical step in forming the collagen-synthetic polymer matrices of the invention involves functionalization, or activation, of the synthetic hydrophilic polymer. The synthetic polymers useful in the present invention are hydrophilic, have at least one and, preferably, two or more functional groups capable of covalently bonding with the lysine residues on a collagen molecule, and are highly pure or purified to a highly pure state such that the polymer is or is treated to become pharmaceutically pure so that it may be injected or implanted into a human patient. Most hydrophilic synthetic polymers can be rendered water-soluble by incorporating a sufficient number of oxygen (or, less frequently, nitrogen) atoms available for forming hydrogen bonds in aqueous solutions. Preferred synthetic polymers are hydrophilic, but not necessarily water-soluble.

All suitable synthetic polymers will be nontoxic, noninflammatory, and nonimmunogenic when administered subcutaneously, and will preferably be essentially nondegradable in vivo over a period of at least several months. The hydrophilic synthetic polymer may increase the hydrophilicity of the conjugate, but does not render it water-soluble. The synthetic polymers can be linear or multiply branched, but are typically not substantially cross-linked.

Although different synthetic hydrophilic synthetic polymers can be used in connection with forming the collagen-synthetic polymer matrices of the invention, the synthetic polymer must be biocompatible, hydrophilic, but relatively insoluble in water, and is preferably one or more forms of derivatized polymeric glycol, preferably, polyethylene glycol (PEG), due to its known biocompatibility. Various forms of derivatized PEG are extensively used in the modification of biologically active molecules because PEG can be formulated to have a wide range of solubilities and because it lacks toxicity, antigenicity, immunogenicity, and does not typically interfere with the enzymatic activities and/or conformations of peptides. Furthermore, PEG is generally non-biodegradable and is easily excreted from most living organisms including humans.

Multifunctionally activated synthetic polymers are most preferred for use in the present invention, with difunctionally activated polymers being most preferred. Multifunctionally activated polymeric glycols preferably have an average molecular weight between about 3000 and 100,000. Difunctionally activated polymeric glycols preferably have an average molecular weight of between about 400 to about 40,000, most preferably about 3000 to about 10,000. Monofunctionally activated polymers may also be used in the practice of the invention. However, because monofunctionally activated synthetic polymers have only one activated functional group, they are capable of covalently conjugating to collagen, but not capable of forming a crosslinked network between collagen molecules.

Multifunctionally activated synthetic polymers can be prepared using various techniques known in the art which provide functionally groups at various locations along the polymer. Difunctionally activated polymeric glycols typically are prepared by constructing reactive hydroxy groups at the ends of the polymer. Multifunctionally activated synthetic polymers are capable of crosslinking the compositions of the invention, and may further be used to attach biologically active molecules to the collagen-synthetic polymer conjugate.

Various functionalized polyethylene glycols have been used effectively in fields such as protein modification (see Abuchowski et al., *Enzymes as Drugs*, John Wiley & Sons: New York, N.Y. (1981) pp. 367–383; and Dreborg et al., *Crit Rev. Therap. Drug Carrier Syst.* (1990) 6: 315), peptide chemistry (see Mutter et al., *The Peptides*, Academic: New York, N.Y. 2: 285–332; and Zalipsky et al., *Int. J. Peptide Protein Res.* (1987) 3: 740), and the synthesis of polymeric drugs (see Zalipsky et al., *Eur. Polym. J.* (1983) 19: 1177; and Ouchi et al., *J. Macromol. Sci. Chem.* (1987) A24: 1011). Various types of conjugates formed by the binding of functionally activated polyethylene glycol with specific pharmaceutically active proteins have been disclosed and found to be useful in medical applications, in part due to the stability of such conjugates with respect to proteolytic digestion, reduced immunogenicity, and longer half-lives within living organisms.

One form of polyethylene glycol is monomethoxy-polyethylene glycol (mPEG), which can be activated by the addition of a compound such as cyanuric chloride, then coupled to a protein (see Abuchowski et al., *J. Biol. Chem,* (1977) 252: 3578). Although such methods of activating polyethylene glycol can be used in connection with the present invention, they are not preferred in that the cyanuric chloride is relatively toxic and must be completely removed from any resulting product in order to provide a pharmaceutically acceptable composition.

Activated forms of PEG can be made from reactants which can be purchased commercially. One form of activated PEG which has been found to be particularly useful in connection with the present invention is PEG-succinate-N-hydroxysuccinimide ester (SS-PEG) (see Abuchowski et al., *Cancer Biochem. Biphys.* (1984) 7: 175). Activated forms of PEG such as SS-PEG react with proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used in connection with the present invention, they are not particularly preferred for use in formed implants intended for long-term use within the human body in that they undergo hydrolysis when subjected to physiological conditions over extended periods of time (see Dreborg et al., *Crit. Rev. Therap. Drug Carrier Syst.* (1990) 6: 315; and Ulbrich et al., *J. Makromol. Chem.* (1986) 187: 1131).

It is possible to link PEG to proteins via urethane linkages, thereby providing a more stable attachment which is more resistant to hydrolytic digestion than the ester linkages (see Zalipsky et al., Polymeric Drug and Drug Delivery Systems, Chapter 10, "Succinimidyl Carbonates of Polyethylene Glycol" (1991)). The stability of urethane linkages has been demonstrated under physiological conditions (see Veronese et al., *Appl. Biochem. Biotechnol.* (1985) 11: 141; and Larwood et al., *J. Labelled Compounds Radiopharm.* (1984) 21: 603). Another means of attaching the PEG to a protein can be by means of a carbamate linkage (see Beauchamp et al., *Anal. Biochem.* (1983) 131: 25; and Berger et al., *Blood* (1988) 71: 1641). The carbamate linkage is created by the use of carbonyldiimidazole-activated PEG. Although such linkages have advantages, the reactions are relatively slow and may take 2 to 3 days to complete.

The various means of activating PEG described above and publications cited in connection with the activation means are described in connection with linking PEG to specific biologically active proteins and not inert, biologically inactive, natural polymers such as collagen. (See *Polymeric Drug and Drug Delivery Systems*, Chapter 10, "Succinimidyl Carbonates of Polyethylene Glycol" (1991).) Such activated PEG compounds can be used in the preparation of covalently crosslinked conjugates of various collagens which can be used in the preparation of a variety of formed implants for use in medical applications.

Specific Forms of Activated PEG

For use in the present invention, polyethylene glycol is modified in order to provide functional groups on one or, preferably, two or more sites along the length of the PEG molecule, so that covalent binding can occur between the PEG and the primary amino groups on a collagen molecule. Some specific activated forms of PEG are shown structurally below, as are generalized reaction products obtained by reacting activated forms of PEG with collagen. In Formulas 1–7, the term COL represents collagen. The term PEG represents polymers having the repeating structure $(OCH_2CH_2)_n$.

The first activated PEG is difunctionally activated PEG succinimidyl glutarate, referred to herein as (SG-PEG). The structural formula of this molecule and the reaction product obtained by reacting it with a collagen are shown in Formula 1.

SG-PEG: Difunctionally Activated PEG Succinimidyl Glutarate

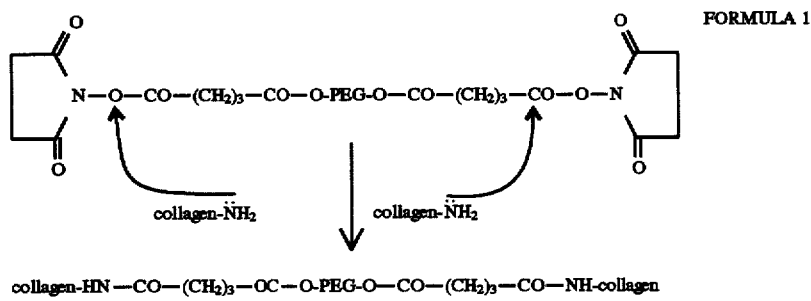

collagen-HN—CO—(CH₂)₃—OC—O-PEG-O—CO—(CH₂)₃—CO—NH-collagen

Another difunctionally activated form of PEG is referred to as PEG succinimidyl (S-PEG). The structural formula for this compound and the reaction product obtained by reacting it with collagen is shown in Formula 2. In any general structural formula for the compounds, the subscript 3 is replaced with an "n". In the embodiment shown in Formula 1, n=3, in that there are three repeating $CH_2$ groups on either side of the PEG. The structure in Formula 2 results in a conjugate which includes an "ether" linkage which is not subject to hydrolysis. This is distinct from the conjugate shown in Formula 1, wherein an ester linkage is provided. The ester linkage is subject to hydrolysis under physiological conditions.

S-PEG, n=3: Difunctionally Activated PEG Succinimidyl

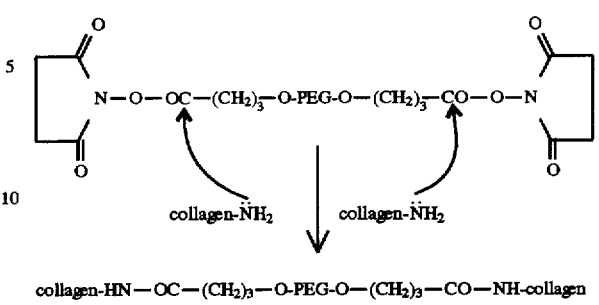

collagen-HN—OC—(CH₂)₃—O-PEG-O—(CH₂)₃—CO—NH-collagen

Yet another difunctionally activated form of polyethylene glycol, wherein n=2, is shown in Formula 3, as is the conjugate formed by reacting the activated PEG with collagen.

S-PEG, n=2: Difunctionally Activated PEG Succinimidyl

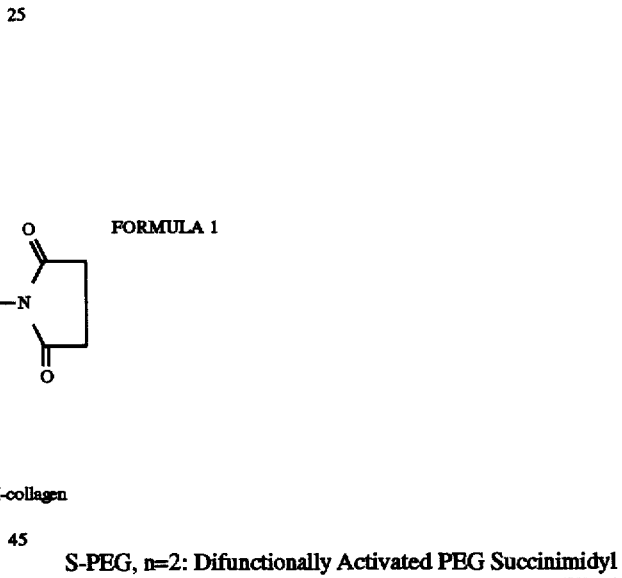

collagen-HN—OC—(CH₂)₂—O-PEG-O—(CH₂)₂—CO—NH-collagen

Another preferred embodiment of the invention similar to the compounds of Formulas 2 and 3 is provided when n=1. The structural formula and resulting collagen-synthetic polymer conjugate are shown in Formula 4. It is noted that this conjugate includes both an ether and a peptide linkage. These linkages are stable under physiological conditions.

S-PEG, n=1: Difunctionally Activated PEG Succinimidyl

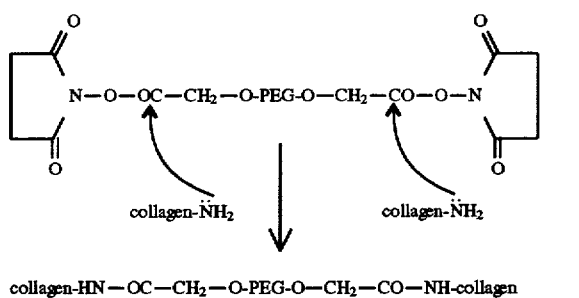

FORMULA 4

Yet another difunctionally activated form of PEG is provided when n=0. This compound is referred to as PEG succinimidyl carbonate (SC-PEG). The structural formula of this compound and the conjugate formed by reacting SC-PEG with collagen is shown in Formula 5.

SC-PEG, n=0: Difunctionally Activated PEG Succinimidyl Carbonate

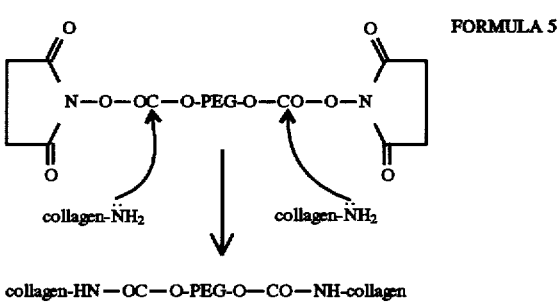

FORMULA 5

All of the activated polyethylene glycol derivatives depicted in Formulas 1–5 involve the inclusion of the succinimidyl group. However, different activating groups can be attached at sites along the length of the PEG molecule. For example, PEG can be derivatized to form difunctionally activated PEG propion aldehyde (A-PEG), which is shown in Formula 6, as is the conjugate formed by the reaction of A-PEG with collagen. The linkage shown in Formula 6 is referred to as a —($CH_2$)$_n$—NH— linkage, where n=1–10.

A-PEG: Difunctionally Activated PEG Propion Aldehyde

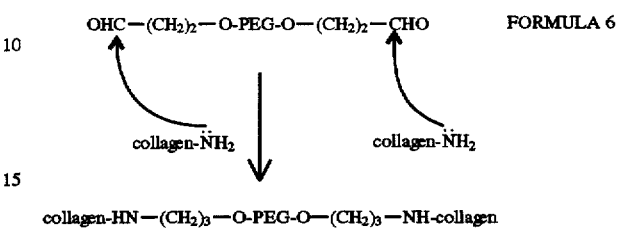

FORMULA 6

Yet another form of activated polyethylene glycol is difunctionally activated PEG glycidyl ether (E-PEG), which is shown in Formula 7, as is the conjugate formed by reacting such with collagen.

E-PEG: Difunctionally Activated PEG Glycidyl Ether

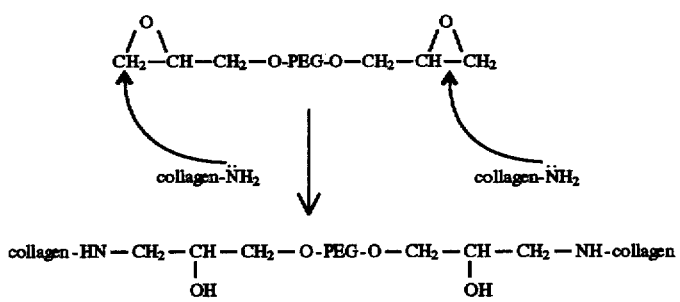

FORMULA 7

Many of the activated forms of polyethylene glycol described above are now available commercially from Shearwater Polymers, Huntsville, Ala. The various activated forms of polyethylene glycol and various linkages which can be used to produce collagen-synthetic polymer conjugates having a range of physical and chemical properties are described in further detail in copending, allowed U.S. application Ser. No. 07/922,541, filed Jul. 2, 1992.

The specific form of functionally activated synthetic hydrophilic polymer used depends on the desired end use of the collagen-synthetic polymer matrix. The type of linkage required between the collagen and the functionally activated polyethylene glycol will depend upon whether the matrix is intended for long- or short-term presence within the body of the patient In general, functionally activated polyethylene glycols which result in ether linkages are preferred for matrices intended for long-term use because these linkages tend to be more resistant to hydrolysis than ester linkages. Polyethylene glycols which result in the weaker ester linkage should be used when it is desired to have short-term presence of the matrix within the body. In fact, ester linkages are preferred for matrices intended to provide localized drug delivery. The covalently bound drug is released from the collagen-synthetic polymer matrix as the ester bonds are hydrolyzed. Combinations of synthetic polymers which result in different linkages can also be employed, as described further below.

Preparation of the Collagen-Synthetic Polymer Matrix

Collagen obtained from any source may be used to prepare the collagen-synthetic polymer matrices of the present invention. Collagen may be extracted and purified from human or other mammalian source, or may be recombinantly or otherwise produced. Collagen of any type may be used, including, but not limited to, types I, II, III, IV, or any combination thereof, although type I is generally preferred. Atelopeptide collagen is generally preferred over telopeptide-containing collagen because of its reduced immunogenicity. Collagens that have been previously crosslinked by radiation, heat, or other chemical crosslinking agents such as glutaraldehyde or carbodiimide are generally not preferred as starting materials. The collagen should be in a pharmaceutically pure form such that it can be incorporated into a human body without generating any significant immune response.

Fibrillar collagen prepared by methods known in the art or commercially available atelopeptide fibrillar collagen compositions, such as Zyderm® I Collagen (35 mg/ml collagen concentration) or Zyderm II Collagen (65 mg/ml collagen concentration), are preferred starting materials to prepare the compositions of the present invention. The collagen concentration of the collagen suspension should generally be within the range of about 10 to about 120 mg/ml, depending on the desired end use application. The collagen concentration of commercially available collagen compositions can be decreased by mixing the collagen composition with an appropriate amount of sterile water or phosphate buffered saline (PBS). Conversely, to increase the collagen concentration, the collagen composition can be concentrated by centrifugation, then adjusted to the desired collagen concentration by mixing with an appropriate amount of sterile water or PBS.

Nonfibrillar collagens may also be used in the practice of the present invention. Nonfibrillar collagens for use in the present invention include collagen-in-solution ("CIS") at pH 2, as well as collagens which have been chemically modified so as to alter the charge distribution on the collagen molecule and, consequently, disrupt the fiber structure of the collagen. Such chemically modified collagens include succinylated collagen and methylated collagen, which may be prepared as disclosed by Miyata et al. in U.S. Pat. No. 4,164,559. Chemically modified, nonfibrillar collagens are more or less optically clear, depending on the degree of chemical modification.

Collagens having controlled fiber size distributions, which may be prepared as described in commonly owned U.S. application serial No. 08/201,860, can also be used to produce the collagen-synthetic polymer matrices of the present invention.

In a general method for preparing the collagen-synthetic polymer matrices of the present invention, collagen is first reacted with a synthetic hydrophilic polymer to form a collagen-synthetic polymer matrix. Synthetic hydrophilic polymers react with primary amino groups found on lysine residues in collagen molecules. For example, type I collagen contains a total of 89 lysine residues. Each of these lysine residues contains one free (unbound) amino group. In addition, there is one primary amino group at the N-terminal of each of the three chains comprising type I collagen. Therefore, each molecule of type I collagen contains a total of 92 (89+3) amino groups available for reaction with synthetic hydrophilic polymers.

The reaction between collagen and the synthetic polymer is generally performed in a controlled manner (i.e., using- a relatively low ratio of synthetic polymer to collagen molecules) so that the degree of crosslinking is limited or maximized, as desired.

The synthetic polymer is preferably a functionally activated polymeric glycol and preferably is a multifunctionally activated polyethylene glycol, most preferably, a difunctionally activated polyethylene glycol. Monofunctionally activated polymers may be used at this stage of the reaction and may in fact be preferred for use in certain embodiments of the invention, as described further below. However, monofunctionally activated polymers are only capable of conjugating single molecules of collagen and are therefore not capable of forming a crosslinked collagen-synthetic polymer network.

The concentration of activated synthetic polymer used in the first step of the reaction will vary depending on the collagen concentration used, the type of activated polymer used (e.g., S-PEG, SG-PEG, etc.), the molecular weight of the activated polymer, and the degree of crosslinking or conjugation desired. For example, when reacting a suspension of collagen having a collagen concentration of approximately 35 mg/ml with a difunctionally activated S-PEG, the concentration of S-PEG used in order to achieve the controlled crosslinking desired in the first step of the reaction is generally within the range of about 1 to about 10 milligrams of difunctionally activated S-PEG per milliliter of collagen suspension. When using a suspension of collagen having a collagen concentration of approximately 65 mg/ml, the concentration of difunctionally activated S-PEG used in the first step of the reaction is generally within the range of about 1 to about 20 milligrams of S-PEG per milliliter of collagen suspension. There are generally a number of primary amino groups remaining on the collagen following the first step reaction.

Chemical Modification of the Collagen-Synthetic Polymer Matrix

Subsequent (ie., second and/or third) steps of the multiple step reaction are largely determined by the desired end use of the resulting composition. However, the second step of the reaction generally involves modification of the remaining primary amino groups on collagen molecules in the matrix. For example, the collagen-synthetic polymer matrix can be further reacted with a second multifunctionally activated polymer to create a more highly crosslinked collagen-synthetic polymer network, or to provide a network wherein there are a number of synthetic polymer molecules having free functional groups available for further conjugation with, for example, biologically active agents or glycosaminoglycans. The second synthetic polymer may be of the same or of a different type than the first synthetic polymer that was used to create the original collagen-synthetic polymer matrix. For example, if a synthetic polymer which results in the formation of an ether linkage between the collagen and polymer is used in the first reaction, it may be desirable to use a synthetic polymer which results in the formation of an ester linkage in the second reaction, or vice versa, if the collagen-synthetic polymer matrix is intended to degrade or partially degrade over time, such as when the matrix is used as a drug delivery system.

The concentration of activated synthetic polymer required in the second step of the reaction is generally approximately equal to, or in excess of, the amount required to achieve complete conjugation of all of the primary amino groups on the collagen, which will vary depending on the collagen concentration used and the type and molecular weight of activated synthetic polymer used. For example, type I collagen contains 92 primary amino groups per molecule and has a molecular weight of approximately 300,000 daltons. Theoretically, 92 molecules of activated synthetic polymer would be required to conjugate all of the primary amino groups on one molecule of type I collagen. For example, when reacting a suspension of type I collagen having a collagen concentration of 35 mg/ml with a synthetic hydrophillic polymer having a molecular weight of 3,755 daltons, 40.3 milligrams of polymer would be required per milliliter of collagen to achieve (theoretically) conjugation of all the primary amino groups on each collagen molecule, as follows:

$$\frac{\text{Polymer conc.(mg/ml)}}{\text{Polymer MW(daltons)}} \times \frac{300{,}000 \text{ daltons}}{\text{Collagen conc.(mg/ml)}} = 92, \text{ or}$$

$$\text{Polymer conc.} = \frac{92(\text{Polymer MW})(\text{Collagen conc.})}{300{,}000 \text{ daltons}}$$

For example:

$$\text{Polymer conc.} = \frac{92(3{,}755 \text{ daltons})(35 \text{ mg/ml})}{300{,}000 \text{ daltons}} = 40.3 \text{ mg/ml}$$

Therefore, in this particular case, a synthetic polymer concentration of at least about 40 milligrams of synthetic polymer per milliliter of collagen suspension (having a collagen concentration of 35 mg/ml) would be used in the second reaction. (The above formula can also be used to determine what percentage of the primary amino groups on the collagen have been conjugated based on the amount of synthetic polymer actually bound to the collagen, as determined, for example, by HPLC.)

Another possibility for a second reaction is to conjugate the collagen-synthetic polymer matrix with a monofunctionally activated synthetic polymer. Although conjugation with a monofunctionally activated polymer will not increase the degree of crosslinking in the matrix, the use of a low molecular weight, monofunctionally activated polymer may serve to "coat" the collagen by binding with primary amino groups that were not conjugated in the first reaction, which may result in a collagen-synthetic polymer matrix having reduced immunogenicity compared with previous collagen-synthetic polymer conjugate compositions. Therefore, if an implant having extremely low immunogenicity is the desired goal, conjugating the crosslinked collagen-synthetic polymer matrix with a monofunctionally activated synthetic polymer should be the second step in the reaction.

The collagen-synthetic polymer matrix formed in the first step of the reaction can also be directly coupled to any biologically active agent, drug, glycosaminoglycan or glycosaminoglycan derivative, etc., that has reactive groups, or can be chemically derivatized to have reactive groups, that are able to bond with remaining primary amino groups on the collagen molecules in the matrix. Coupling biologically active molecules to the collagen-synthetic polymer matrix provides an effective sustained release drug delivery system, or can serve to biologically "anchor" the collagen-synthetic polymer matrix to host tissue. The amount of biologically active agent required to be therapeutically effective is dependent on the specific agent used. Coupling glycosaminoglycans or their derivatives to the collagen-synthetic polymer matrix results in implant compositions having novel physical and chemical characteristics, depending on the type of glycosaminoglycan used and the relative amounts of collagen and glycosaminoglycan in the composition. Glycosaminoglycans for use in the present invention include hyaluronic acid, chondroitin sulfate A, chondroitin sulfate C, dermatan sulfate, keratan sulfate, keratosulfate, chitin, chitosan, heparin, and derivatives thereof. For example, glycosaminoglycans such as heparin have unique anticoagulation properties which make them very desirable for use in or on any blood-contacting implant or device, such as a vascular graft or artificial organ.

The collagen-synthetic polymer matrix can also be further crosslinked by means of any of a number of conventional chemical crosslinking agents, including, but not limited to, glutaraldehyde, divinyl sulfone, epoxides, carbodiimides, and imidazole. The concentration of chemical crosslinking agent required is dependent on the specific agent being used and the degree of crosslinking desired.

Yet another possibility for modification of the collagen-synthetic polymer matrix is to bind amino acids or peptides to the collagen in the matrix by first coupling the amino acid or peptide to a difunctionally activated synthetic polymer, then reacting it with the preformed collagen-synthetic polymer matrix. Alternatively, the amino acid or peptide can be chemically modified to have functional groups capable of reacting with available amino groups on collagen molecules in the matrix. Said amino acids or peptides can serve as attachment points to bind other polymers, which have been chemically derivatized to react directly with amino acid moieties, to the matrix. Such polymers include, without limitation, glycosaminoglycans, poly(N-acetyl glycosamine), and poly(alkylene oxides) such as polyethylene glycol, polypropylene oxide, polybutylene oxide, etc..

Another option is to modify the collagen in the collagen-synthetic polymer matrix by means of various chemical reactions, such as esterification, amidation, or acylation, depending on the desired end use of the matrix. Esterification can be accomplished by reacting the collagen-synthetic polymer matrix with any suitable esterifying agent, such as methanol, ethanol, or butanol. Amidation can be accomplished by reacting the matrix with any suitable amidating agent, such as glutaric anhydride or succinic anhydride. Acylation can be accomplished by reacting the matrix with a suitable acylating agent, such as benzoylchloride or butyrylchloride. Any reaction that results in an alteration of the charge distribution on the collagen will cause a disruption of the collagen fiber structure, resulting in biomaterials which are more or less transparent, depending on the degree to which the collagen has been chemically modified.

Commonly owned, copending U.S. application Ser. No. 08/147,227, disclosed the conjugation of synthetic hydrophilic polymers to collagens which had been previously chemically modified to be nonfibrillar, such as methylated collagen or succinylated collagen. However, nonfibrillar collagen is very viscous. Due to its high viscosity, mixing the nonfibrillar collagen with synthetic hydrophilic polymers can be rather difficult, resulting in a non-uniformly crosslinked collagen-synthetic polymer matrix, which is not desirable when preparing, for example, preformed or in situ crosslinked lenticules for long-term use on the eye. Fibrillar collagen, on the other hand, is less viscous, more elastic, generally easier to handle, and more easily mixed with synthetic hydrophilic polymers than nonfibrillar collagen. It is therefore advantageous, when preparing an ophthalmic (or any other optically clear) device, to use fibrillar collagen as the starting material, mix the collagen with a synthetic hydrophilic polymer to form a collagen-synthetic polymer matrix, then chemically modify the resulting collagen-synthetic polymer matrix, such as by esterification or amidation, to produce an optically transparent implant In another method for preparing optically clear collagen-synthetic polymer matrices, nonfibrillar collagen, such as CIS, having a pH of about 3 or less is neutralized to pH 7, then immediately reacted with a monofunctionally activated synthetic polymer to prevent fiber formation from occurring, resulting in the formation of an optically clear collagen-synthetic polymer conjugate. The resulting collagen-synthetic polymer conjugate is able to be extruded through a fine gauge needle because it does not contain the intermolecular crosslinks obtained when a multifunctionally activated polymer is used. The clear collagen-synthetic polymer conjugate can subsequently be crosslinked using a multifunctionally activated synthetic polymer, to provide an optically clear collagen-synthetic polymer matrix.

Further (Third-Step) Modification of the Collagen-Synthetic Polymer Matrix

A collagen-synthetic polymer matrix that has been modified according to one or more of the reactions described above can be subjected to a third-step reaction in which biologically active molecules or glycosaminoglycans are covalently bound to the matrix by means of the remaining active groups on the synthetic polymer molecules that are covalently bound to the matrix.

Commonly owned U.S. Pat. No. 5,162,430 disclosed the binding of biologically active agents to synthetic polymer molecules, then reacting with collagen to form a three-part collagen-synthetic polymer-active agent conjugate. However, when binding the biologically active agent to the synthetic polymer, a large excess of polymer molecules had to be used in order to obtain a majority of conjugates comprising active agent-synthetic polymer-X (where X is a free functional group on the synthetic polymer molecule) and to reduce the possibility of obtaining active agent-synthetic polymer-active agent conjugates, which are inactive and, furthermore, have no remaining active groups to bind to the collagen matrix. The active agent-synthetic polymer-X conjugates were subsequently mixed with collagen to form active agent-synthetic polymer-collagen conjugates.

The above process was inefficient because some of the active agents still formed active agent-synthetic polymer-active agent conjugates. Also, it was difficult to produce matrices having high biological activity, because the concentration of active agent needed to be low relative to the concentration of synthetic polymer in order to avoid formation of the active agent-synthetic polymer-active agent conjugates. Combining the biologically active agent, synthetic polymer, and collagen at the same time proved to be even more inefficient because of the relatively large number of active agent-synthetic polymer-active agent conjugates formed.

In a particularly preferred embodiment of the present invention, collagen is covalently bound, preferably by means of an ether linkage, to a synthetic hydrophilic polymer, which is preferably a difunctionally activated polyethylene glycol, to form a crosslinked collagen-synthetic polymer matrix. The collagen-synthetic polymer matrix is further modified by covalently binding, preferably by means of an ester linkage, a second synthetic hydrophilic polymer, which is preferably a difunctionally activated polyethylene glycol, to the remaining primary amino groups on the collagen. (Any unreacted synthetic polymer can be washed off the collagen-synthetic polymer matrix at this point.) In a third step, biologically active agents (or glycosaminoglycans or their derivatives) are covalently bound to any remaining active ends of synthetic polymers which are bound by one functional group to the collagen-synthetic polymer matrix. The above process is a very efficient method for producing biologically active matrices in that the possibility of obtaining active agent-synthetic polymer-active agent conjugates is avoided, because at least one end of each polymer molecule is already bound to a collagen molecule.

USE AND ADMINISTRATION

The collagen-synthetic polymer matrices of the present invention can be used to prepare implants for use in a variety of medical applications, such as vascular grafts, artificial organs, and heart valves. In a general method for preparing formed implants, collagen and a multifunctionally activated synthetic polymer are mixed and cast or molded into the desired size and shape before substantial crosslinking has occurred between the collagen and the polymer. The collagen and synthetic polymer are allowed to incubate and crosslink to achieve the desired size and shape. Once the first step of the crosslinking reaction has been completed, the formed implant can be further crosslinked using multifunctionally activated synthetic polymers or conventional chemical crosslinking agents, conjugated using monofunctionally activated synthetic polymers, and/or coupled to biologically active agents. The second step reaction can be accomplished by, for example, immersing the implant in a solution of the desired agent. For example, when preparing implants for use in contact with blood, such as vascular grafts or artificial heart valves, it may be advantageous to couple an antithrombotic agent or an agent which prevents platelet adhesion to the implant Conjugating biologically active agents to the implant in such a manner results in most of the biologically active agents being distributed along the surfaces of the implant, where they can exert their greatest therapeutic effect. Conjugating the implant with monofunctionally activated synthetic polymers may serve to reduce thrombosis or platelet adhesion by "smoothing out" the surface of the implant and making it less immunogenic or reactive in general.

Tubes made from the collagen-synthetic polymer matrices of the present invention can be used as vascular grafts or stents, or as replacements for any other damaged or defective nonvascular lumen within the body, such as in the reproductive or urological systems, for example, damaged fallopian tubes or ureters. Methods for making collagen-synthetic polymer tubes for use in various applications are described further in U.S. Pat. No. 5,292,802.

The collagen-synthetic polymer matrices of the present invention can also be used to coat synthetic implants for implantation within the body, including, without limitation, bone and joint prostheses, coiled platinum wires for treating aneurysms, breast implants, catheters, artificial organs, vascular grafts (such as Dacron® or Teflon® grafts) and stents, sutures, and artificial ligaments or tendons. The implant is coated with a solution containing collagen and synthetic polymer before substantial crosslinking has been achieved between the collagen and the polymer. The collagen and synthetic polymer are allowed to crosslink on the surface of the implant Once the first step of the crosslinking reaction has been completed, the implant can be further crosslinked using multifunctionally activated synthetic polymers or conventional chemical crosslinking agents, conjugated using monofunctionally activated synthetic polymers, and/or coupled to biologically active agents. For example, a synthetic vascular graft may first be coated with a collagen-synthetic polymer conjugate composition, which may subsequently be coupled to antithrombotic agents, anti-platelet adhesion agents, or glycosaminoglycans having anticoagulation properties, such as heparin. In the case of a bone implant, it may be advantageous to couple to the collagen-synthetic polymer coating on the implant bone morphogenic proteins or osteogenic factors which promote the growth of new bone around the implant and/or otherwise facilitate the incorporation of the implant within the host tissue. Methods for coating implants with collagen-synthetic polymer conjugates are described in further detail in copending U.S. application Ser. No. 07/984,933, filed Dec. 2, 1992.

In one preferred embodiment, a mixture of collagen and a synthetic hydrophilic polymer, in an amount sufficient to allow limited crosslinking to occur, is applied to the surface of the object to be coated before substantial crosslinking has occurred. Crosslinking of the collagen and the synthetic polymer is allowed to occur on the surface of the implant, following which the implant is immersed in a solution of a second synthetic hydrophilic polymer. In a third-step reaction, a substance such as a biologically active agent or a glycosaminoglycan is allowed to react with remaining functional groups on synthetic polymers bound to the collagen-synthetic polymer matrix which has been coated on the implant. This process allows for implants to be efficiently prepared such that biologically active agents are distributed on the surfaces of the implant where they can exert their greatest therapeutic effect.

For example, in a specific preferred embodiment for preparing coated vascular grafts or stents, collagen and an activated synthetic polymer are combined in a relatively low ratio of synthetic polymer to collagen in order to form a partially crosslinked collagen-synthetic polymer matrix and, prior to the occurrence of substantial crosslinking, cast into the shape of a tube to form a partially crosslinked collagen-synthetic polymer tube. The resulting tube is then fitted into the interior of a synthetic stent, such as that formed from a metallic wire. A second partially crosslinked collagen-synthetic polymer tube is formed and placed on the outer surface of the stent.

The two collagen-synthetic polymer tubes need not have the same properties. For example, in a second-step reaction after forming the partially crosslinked collagen-synthetic polymer matrix, the outer tube could be covalently bound to a biologically active agent, such as a growth factor such as TGF-beta, to encourage incorporation of the stent into the surrounding tissue. The collagen-synthetic polymer matrix of the inner tube could be covalently bound to an antithrombogenic agent, such as heparin, to prevent blood from clotting on the inner surface of the stent. Accordingly, synthetic hydrophilic polymers which form different types of linkages when bound to collagen could be used to form the inner and outer tubes. For example, the collagen matrix of the outer tube may be bound by means of a synthetic polymer which results in the formation of an ester linkage between the collagen and the synthetic polymer. As such, the bonds between the collagen and the synthetic polymer will slowly hydrolyze as the exterior surface of the stent is incorporated into the surrounding tissue over time. Conversely, the collagen matrix of the inner tube may be bound by means of a synthetic polymer which results in the formation of an ether linkage, as it is important that the inner surface of the stent remain stable and unreactive for a long period of time.

The entire collagen-synthetic polymer-coated stent structure is then placed or dipped in a solution of a functionally activated synthetic hydrophilic polymer, which may be of the same or of a different type than that used to form either of the two collagen-synthetic polymer tubes. The interior and exterior collagen-synthetic polymer tubes are then allowed to crosslink with each other to form a single, continuous surface by means of the openings in the stent.

The collagen-synthetic polymer matrices of the invention can further be used specifically as localized drug delivery systems. The desired therapeutic agent can be coupled directly to the collagen-synthetic polymer matrix, which can then implanted in the body at the site in need of therapy, such as a wound or tumor. The therapeutic agents will be released from the matrix as the covalent bonds between the agents and the matrix are slowly broken down by enzymatic degradation. In such a situation, it may be advantageous to use a synthetic polymer which results in an ether linkage when forming the collagen-synthetic polymer matrix in the first reaction, so that the matrix itself is relatively stable and resistant to hydrolytic degradation. The therapeutic agent itself may be coupled to the matrix in the second reaction by means of a synthetic polymer which forms an ester linkage, resulting in a continuous release of the agent as the ester bonds between the agent and synthetic polymer hydrolyze over time. Alternatively, a mixture of synthetic polymers, some which result in the ether linkage and some which result in the ester linkage, can be used to couple the agents to the matrix, so that some of the agents are released in a sustained manner, and some of the agents remain tethered to the matrix, remaining active and providing a biological effect on the natural substrate for the active site of the protein.

Optically clear collagen-synthetic polymer matrices can also be prepared by applying the multiple step reactions of the present invention. Such matrices may be used in a variety of ophthalmic applications, as described further below, or in any therapeutic application where an optically clear material is desirable. In one method for producing an optically clear collagen-synthetic polymer matrix, collagen is first reacted with a multifunctionally activated synthetic polymer to produce an optically clear, crosslinked collagen-synthetic polymer matrix, which can be molded or otherwise shaped to form an ophthalmic implant such as a preformed lenticule or an artificial cornea or lens. The collagen-synthetic polymer matrix can then be chemically modified by, for example, esterification or amidation to reduce the ionic interactions between collagen molecules, resulting in a collagen-synthetic polymer matrix which is more or less transparent, depending on the degree of chemical modification of the matrix.

Alternatively, nonfibrillar collagen, such as CIS, having a pH of about 3 or less can be neutralized to pH 7, then immediately reacted with a monofunctionally activated synthetic polymer to prevent fiber formation from occurring, resulting in the formation of an optically clear collagen-synthetic polymer conjugate. The resulting collagen-synthetic polymer conjugate is able to be extruded through a fine gauge needle because it does not contain the intermolecular crosslinks obtained when a multifunctionally activated polymer is used. The clear collagen-synthetic polymer conjugate can subsequently be crosslinked using a multifunctionally activated synthetic polymer, such as in the formation of an in situ polymerizable lenticule on the cornea of an eye.

The multiple step techniques described above to prepare optically clear collagen-synthetic polymer matrices may also be used to prepare membranes for use in a variety of applications, such as wound healing, drug delivery, or adhesion prevention. For example, a suspension of fibrillar collagen is mixed with a multifunctionally activated synthetic polymer, then cast as a thin layer on the bottom of a flat sheet container before substantial crosslinking has occurred between the collagen and the polymer. The resulting thin membrane is further reacted with a monofunctionally activated synthetic polymer in order to coat any remaining reactive groups on the collagen with synthetic polymer and then, optionally, lyophilized. Various wound healing agents, such as TGF-beta, or drugs, such as antiinflammatories or antibiotics, may be coupled to the collagen-synthetic polymer membrane. Factors which prevent tissue ingrowth between organs may be coupled to membranes for use in adhesion prevention.

In an alternative method for forming membranes, collagen is first reacted with a monofunctionally activated synthetic polymer. The resulting collagen-synthetic polymer conjugate can be extruded to form a membrane in situ, then subsequently crosslinked using a multifunctionally activated synthetic polymer.

EXAMPLES

The following examples are put forth so as to provide those of ordinary skill in the art with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1
(Preparation of PEG-Collagen Matrices Using Single Step Reaction)

Samples were prepared as follows: One (1) milliliter of Zyderm® I Collagen (35 mg/ml collagen concentration, available from Collagen Corporation, Palo Alto, Calif.) was mixed with 1.5 mg, 5 mg, or 10 mg of dry, difunctionally activated S-PEG (3,755 MW) by syringe-to-syringe mixing, using approximately 40–50 passes to ensure that mixing was complete. The samples had S-PEG concentrations of 1.5, 5.0, and 10.0 mg PEG per ml collagen, respectively. The samples were incubated in their respective syringes at 37° C. for 16 hours. The resulting PEG-collagen crosslinked matrices were pushed out of the large end of the syringes. Each of the three 1-ml cylindrical matrices was cut in half. One-half of each PEG-collagen matrix was put back into its respective syringe for further experimentation.

Each of the three remaining 0.5-ml matrices was washed with water to remove any unreacted PEG. The water containing unreacted PEG for each sample was retained.

The PEG-collagen matrices were then placed in 1M NaOH at 65°–70° C. for 1 hour to hydrolyze the bound PEG. Hydrolysis was performed in order to break the covalent bonds between the collagen and the bound PEG so that the amount of PEG actually bound to the collagen could subsequently be quantified by HPLC, as described in Example 2, below. The PEG was extracted from each of the three 0.5-ml samples using $CHCl_3$. The $CHCl_3$ was subsequently evaporated under $N_2$. The PEG residue was then dissolved in water.

Example 2
(Quantification of Bound PEG in PEG-Collagen Matrices Prepared Using Single Step Reaction)

The samples containing the unreacted PEG and previously bound (hydrolyzed) PEG obtained from the PEG-collagen matrices prepared using the single step reaction, as described in Example 1, above, were analyzed in triplicate by HPLC in order to quantify the amount of PEG that had been bound to the collagen. HPLC analysis of PEG samples was performed using an isocratic elution. Conditions of HPLC analysis were as follows:

| Column: | Waters Ultrahydrogel 250 |
|---|---|
| Pore Size: | 250 Angstroms |
| Column Size: | 7.8 mm × 30 cm |
| Exclusion Limit: | $8 \times 10^4$ daltons |
| Injection Volume: | 20 µl |
| Mobile Phase: | 5 mM Sodium Acetate buffer, pH = 5.5 at 21° C. |
| Flow Rate: | 0.5 ml/min |
| Pressure: | 0.8 mPa |
| Detector: | Dual Detector System, Refractive Index & UV at 260 nm |

An external standard calibration curve was obtained using PEG solutions of various concentrations. The stock solution was prepared by dissolving 10.0 mg of difunctionally activated S-PEG in 1.000 ml of deionized water. The solution was sequentially diluted to 5.00, 2.50, 1.25, 0.625, and 0.3125 mg/ml and analyzed by HPLC. Integrating the peak at a retention time of 16 minutes, the peak area was plotted against each concentration of PEG standard.

FIGS. 1–3 show the relative amounts of unreacted PEG and bound PEG as a percentage of the total amount of PEG added to the collagen for the PEG-collagen matrices having S-PEG concentrations of 1.5, 5.0, and 10.0 mg/ml, respectively..

As shown in FIG. 1, the sample having an S-PEG concentration of 1.5 mg/ml contained no unreacted S-PEG. As shown in FIG. 2, the sample having an S-PEG concentration of 5.0 mg/ml contained a small amount (about 10–15%) of unreacted S-PEG. As shown in FIG. 3, the sample having an S-PEG concentration of 10.0 mg/ml showed a slightly higher amount of unreacted S-PEG, about 20% of the total amount of S-PEG originally added to the collagen.

Example 3
(Preparation of PEG-Collagen Matrices Using Two-Step Reaction)

The 0.5-ml PEG-collagen matrices which had been put back in their syringes were then extruded through the needle ends of their respective syringes to break the matrices into small pieces. The broken matrices were placed into test tubes and 100 mg of difunctionally activated S-PEG, dissolved in approximately 1–2 ml of PBS, was added to each of the three test tubes. The test tubes containing the broken PEG-collagen matrices and excess PEG were incubated at 37° C. for approximately 16 hours.

Each of the three PEG-collagen matrices was washed with water to remove any unreacted PEG. The PEG-collagen matrices were then placed in 1M NaOH at 65°–70° C. for 1 hour to hydrolyze the bound PEG. Hydrolysis was performed in order to break the covalent bonds between the collagen and the bound PEG so that the amount of PEG actually bound to the collagen could subsequently be quantified by HPLC, as described in Example 4, below. The PEG was extracted from each of the three samples using $CHCl_3$. The $CHCl_3$ was subsequently evaporated under $N_2$. The PEG residue from each sample was then dissolved in water.

Example 4
(Quantification of Bound PEG in PEG-Collagen Matrices Prepared Using Two-Step Reaction)

The samples containing the previously bound (hydrolyzed) PEG obtained from the PEG-collagen matrices prepared using the two-step reaction, as described in Example 3, above, were analyzed in triplicate by HPLC, using the same conditions described in Example 2, in order to quantify the amount of PEG that had been bound to the collagen. FIGS. 4-6 show the actual amounts (in milligrams) of bound PEG found in the PEG-collagen matrices prepared using the two-step reaction, compared to matrices prepared using the single step reaction, for PEG-collagen matrices having original S-PEG concentrations of 1.5, 5.0, and 10.0 mg/ml, respectively.

Each collagen molecule contains 92 primary amino groups available for reaction with functionally activated synthetic polymers. Theoretically, therefore, 92 molecules of PEG should be able to conjugate with the 92 primary amino groups residues on one collagen molecule. An S-PEG concentration of 1.5 mg per ml of collagen represents about 3.6 molecules of S-PEG per molecule of collagen. Therefore, there are still a large number of lysine residues available for further crosslinking with the excess (100 mg) PEG that was added in the second step of the crosslinking reaction. As shown in FIG. 4, the PEG-collagen matrix having an original S-PEG concentration of 1.5 mg/ml contained approximately 16-17 mg of S-PEG per 0.5-ml matrix following the second step of the reaction, representing approximately 76-80 molecules of S-PEG per molecule of collagen.

As shown in FIG. 7, of the three S-PEG concentrations evaluated during this experiment (1.5, 5.0, and 10.0 mg S-PEG per ml collagen), PEG-collagen matrices having an S-PEG concentration of 5.0 mg/ml show the best gel strength (as measured using the Instron Model 4202), indicating that an optimum level of crosslinking between the PEG and the collagen has been achieved at this S-PEG concentration. An S-PEG concentration of 5.0 mg per ml of collagen represents about 12 molecules of S-PEG per molecule of collagen. As shown in FIG. 5, the PEG-collagen matrix having an original S-PEG concentration of 5.0 mg/ml contained approximately 10-11 mg of S-PEG per 0.5-ml matrix following the second step of the crosslinking reaction, representing approximately 48-52 molecules of S-PEG per molecule of collagen. Because of the tightly crosslinked PEG-collagen network achieved at an S-PEG concentration of 5.0 mg/ml, steric hindrance may prevent binding of much additional S-PEG to the collagen matrix, which would explain why the PEG-collagen matrices having an original S-PEG concentration of 5.0 mg/ml would contain a smaller amount of bound S-PEG after the second crosslinking reaction than the matrices which had an original S-PEG concentration of only 1.5 mg/ml.

As shown in FIG. 6, the PEG-collagen matrix having an original S-PEG concentration of 10.0 mg/ml contained approximately 24-25 mg of S-PEG per 0.5-ml following the second step of the crosslinking reaction, representing approximately 96-100 molecules of S-PEG per molecule of collagen. As shown in FIG. 7, PEG-collagen matrices having an S-PEG concentration of 10.0 mg/ml show a gel strength approximately equal to that of PEG-collagen matrices having an S-PEG concentration of 1.5 mg/ml, and significantly less than that of PEG-collagen matrices having an S-PEG concentration of 5.0 mg/ml. An S-PEG concentration of 10.0 mg per ml of collagen represents about 24 molecules of S-PEG per molecule of collagen. At this S-PEG concentration, many of the difunctionally activated S-PEG molecules are simply conjugated to one collagen molecule each, thereby eliminating available crosslinking sites on the collagen molecule and rendering the S-PEG technically monofunctional (with regards to further reaction). This phenomenon causes the creation of a looser crosslinked PEG-collagen network.

Because of this, much additional S-PEG was allowed to bind to the PEG-collagen network during the second-step crosslinking reaction, in spite of the large amount of PEG already bound. The looser network created by the high original PEG concentration in the matrix prevented the steric hindrance that was believed to have occurred with the more optimally crosslinked 5.0 mg/ml PEG-collagen matrix. Because many of the S-PEG molecules were bound to only one collagen molecule instead of two, there were still a large number of primary amino groups available for further conjugation with PEG.

Loosely crosslinked collagen-synthetic polymer networks are desirable in a variety of applications. For example, these matrices are ideal for delivery of biologically active agents, because they contain many synthetic polymer molecules that are bound to the collagen-synthetic polymer matrix by only one functional group (rather than crosslinking two collagen molecules by binding one collagen molecule with each of its two functional groups) and therefore have another functional group available for binding a biologically active molecule, such as a growth factor or other drug. Conversely, glycosaminoglycans can also be bound to the PEG-collagen matrix in such a manner.

Loosely crosslinked collagen-synthetic polymer networks prepared as described above are also useful in applications where in situ crosslinking of the collagen-synthetic polymer implant to host tissue is desired, because of the many free functional groups on the synthetic polymer molecules that are available for binding to host collagen molecules.

What is claimed is:

1. A collagen-synthetic polymer matrix carrying a biologically active agent, a glycosaminoglycan or a glycosaminoglycan derivative prepared by a process comprising the steps of:

(a) covalently binding collagen with a first multifunctionally activated synthetic hydrophilic polymer to form a covalently binding collagen-synthetic polymer matrix intermediate;

(b) further reacting the covalently binding collagen-synthetic polymer matrix intermediate with a first chemical substance to form a modified collagen-synthetic polymer matrix, wherein the first chemical substance is selected from the group consisting of a second synthetic hydrophilic polymer, a chemical crosslinking agent, an esterifying agent, an amidating agent, an acylating agent, a functionally activated amino acid and a functionally activated peptide; and (c) binding a second chemical substance to the modified covalently binding collagen-synthetic polymer matrix, wherein the second chemical substance is selected from the group consisting of a biologically active agent, a glycosaminoglycan and a glycosaminoglycan derivative.

2. A collagen-synthetic polymer matrix prepared by a process comprising the steps of:

(a) covalently binding collagen with a first multifunctionally activated crosslinking agent consisting of a synthetic hydrophilic polymer covalently binding to form a collagen-synthetic polymer matrix intermediate;

(b) further crosslinking the covalently binding collagen-synthetic polymer matrix intermediate with a second multifunctionally activated crosslinking agent to form a modified covalently binding collagen-synthetic polymer matrix, wherein the second multifunctionally activated crosslinking agent is selected from the group consisting of a second synthetic hydrophilic polymer and a chemical crosslinking agent; and (c) binding a biologically active agent to the second multifunctionally activated crosslinking agent in the modified covalently binding collagen-synthetic polymer matrix.

3. A collagen-synthetic polymer matrix carrying a biologically active agent, a glycosaminoglycan or a glycosaminoglycan derivative prepared by a process comprising the steps of:

(a) covalently binding reacting collagen with a first multifunctionally activated synthetic hydrophilic polymer to form a covalently binding collagen-synthetic polymer matrix intermediate;

(b) further reacting the covalently binding collagen-synthetic polymer matrix intermediate with a second synthetic hydrophilic polymer to form a modified covalently binding collagen-synthetic polymer matrix; and (c) binding a substance to the modified collagen-synthetic polymer matrix, wherein the substance is selected from the group consisting of a biologically active agent, a glycosaminoglycan and a glycosaminoglycan derivative.

4. The collagen-synthetic polymer matrix of any one of claims 1 to 3, wherein the collagen is atelopeptide fibrillar collagen.

5. The collagen-synthetic polymer matrix of claim 4, wherein the first synthetic hydrophilic polymer and/or the second synthetic hydrophilic polymer is a functionally activated polymeric glycol.

6. The collagen-synthetic polymer matrix of claim 5, wherein the functionally activated polymeric glycol is a difunctionally activated polyethylene glycol.

7. The collagen-synthetic polymer matrix of claim 3, wherein the collagen and the first and/or the second synthetic hydrophilic polymer are covalently bound to each other by a linkage selected from the group consisting of an ether linkage, an ester linkage, and a urethane linkage.

8. The collagen-synthetic polymer matrix of claim 1, wherein the first chemical substance is a second synthetic hydrophilic polymer.

9. The collagen-synthetic polymer matrix of claim 8, wherein the second synthetic hydrophilic polymer is selected from the group consisting of a difunctionally activated polymeric glycol and a monofunctionally activated polyethylene glycol.

10. The collagen-synthetic polymer matrix of claim 2, wherein the second chemical substance is a biologically active agent.

11. The modified collagen-synthetic polymer matrix of claim 3, wherein the second chemical substance is a glycosaminoglycan or a glycosaminoglycan derivative.

12. The collagen-synthetic polymer matrix of claim 1, wherein the second chemical substance is a biologically active agent.

13. The collagen-synthetic polymer matrix of claim 12, wherein the biologically active agent is selected from the group consisting of a growth factor, a cytokine, an antibiotic, an antiinflammatory agent, an antithrombotic agent and a peptide.

14. The collagen-synthetic polymer matrix of claim 1, wherein the second chemical substance is a glycosaminoglycan or a glycosaminoglycan derivative.

15. The collagen-synthetic polymer matrix of claim 14, wherein the second chemical substance is a glycosaminoglycan selected from the group consisting of hyaluronic acid, chondroitin sulfate A, chondroitin sulfate C, dermatan sulfate, keratan sulfate, keratosulfate, chitin, chitosan and heparin.

16. The collagen-synthetic polymer matrix of claim 1, wherein the first chemical substance is a chemical crosslinking agent.

17. The collagen-synthetic polymer matrix of claim 16, wherein the chemical crosslinking agent is selected from the group consisting of glutaraldehyde, formaldehyde, divinyl sulfone, a carbodiimide, an epoxide and an imidazole.

18. The collagen-synthetic polymer matrix of claim 1, wherein the first chemical substance is an esterifying agent.

19. The collagen-synthetic polymer matrix of claim 18, wherein the esterifying agent is selected from the group consisting of methanol, ethanol, propanol and butanol.

20. The collagen-synthetic polymer matrix of claim 1, wherein the first chemical substance is an amidating agent.

21. The collagen-synthetic polymer matrix of claim 20, wherein the amidating agent is selected from the group consisting of glutaric anhydride and succinic anhydride.

22. The collagen-synthetic polymer matrix of claim 1, wherein the first chemical substance is an acylating agent.

23. The collagen-synthetic polymer matrix of claim 22, wherein the acylating agent is selected from the group consisting of benzoylchloride and butyrylchloride.

24. The collagen-synthetic polymer matrix of claim 3, wherein the collagen and the first synthetic hydrophilic polymer are covalently bound to each other by an ether linkage, and the collagen and the second synthetic hydrophilic polymer are covalently bound to each other by an ester linkage.

25. A process for preparing a collagen-synthetic polymer matrix carrying a biologically active agent, a glycosaminoglycan or a glycosaminoglycan derivative comprising the steps of:

(a) covalently binding reacting collagen with a first multifunctionally activated synthetic hydrophilic polymer to form a covalently binding collagen-synthetic polymer matrix intermediate;

(b) further reacting the covalently binding collagen-synthetic polymer matrix intermediate with a first chemical substance to form a modified covalently binding collagen-synthetic polymer matrix, wherein the first chemical substance is selected from the group consisting of a second synthetic hydrophilic polymer, a chemical crosslinking agent, an esterifying agent, an amidating agent, an acylating agent, a functionally activated amino acid and a functionally activated peptide; and (c) binding a second chemical substance to the modified covalently binding collagen-synthetic polymer matrix, wherein the second chemical substance is selected from the group consisting of a biologically active agent, a glycosaminoglycan and a glycosaminoglycan derivative.

26. A process for preparing a collagen-synthetic polymer matrix comprising the steps of:

(a) covalently binding reacting collagen with a first multifunctionally activated crosslinking agent consisting of a synthetic hydrophilic polymer to form a covalently binding collagen-synthetic polymer matrix intermediate;

(b) further crosslinking the covalently binding collagen-synthetic polymer matrix intermediate with a second multifunctionally activated crosslinking agent to form a modified covalently binding collagen-synthetic polymer matrix, wherein the second multifunctionally activated crosslinking agent is selected from the group consisting of a second synthetic hydrophilic polymer and a chemical crosslinking agent; and (c) binding a biologically active agent, a glycosaminoglycan or a glycosaminoglycan derivative to the second multifunctionally activated crosslinking agent in the modified covalently binding collagen-synthetic polymer matrix.

27. The process of claim 26, wherein a biologically active agent is bound to the second multifunctionally activated crosslinking agent.

28. The process of claim 26, wherein a glycosaminoglycan or a glycosaminoglycan derivative is bound to the second multifunctionally activated crosslinking agent.

29. A process for preparing a collagen-synthetic polymer matrix carrying a biologically active agent, a glycosaminoglycan or a glycosaminoglycan derivative comprising the steps of:

(a) covalently binding collagen with a first multifunctionally activated synthetic hydrophilic polymer to form a covalently binding collagen-synthetic polymer matrix intermediate;

(b) further reacting the covalently binding collagen-synthetic polymer matrix intermediate with a second synthetic hydrophilic polymer to form a covalently binding modified collagen-synthetic polymer matrix; and (c) binding a biologically active agent, a glycosaminoglycan or a glycosaminoglycan derivative to the modified collagen-synthetic polymer matrix.

30. The process of any one of claims 25 to 29, wherein the collagen is atelopeptide fibrillar collagen.

31. The process of any one of claims 25 to 29, wherein the first and/or the second synthetic hydrophilic polymer is a functionally activated polymeric glycol.

32. The process of claim 31, wherein the functionally activated polymeric glycol is a difunctionally activated polyethylene glycol.

33. The process of claim 29, wherein the collagen and the first and/or the second synthetic hydrophilic polymer are covalently bound to each other by a linkage selected from the group consisting of an ether linkage, an ester linkage and a urethane linkage.

34. The process of claim 25, wherein the first chemical substance is a second synthetic hydrophilic polymer.

35. The process of claim 34, wherein the second synthetic hydrophilic polymer is selected from the group consisting of a difunctionally activated polyethylene glycol and a monofunctionally activated polyethylene glycol.

36. The process of claim 25, wherein the second chemical substance is a biologically active agent.

37. The process of claim 27 or 36, wherein the biologically active agent is selected from the group consisting of a growth factor, a cytokine, an antibiotic, an antiinflammatory agent, an antithrombotic agent and a peptide.

38. The process of claim 25, wherein the second chemical substance is a glycosaminoglycan or a glycosaminoglycan derivative.

39. The process of claim 25, wherein the second chemical substance is a glycosaminoglycan selected from the group consisting of hyaluronic acid, chondroitin sulfate A, chondroitin sulfate C, dermatan sulfate, keratan sulfate, keratosulfate, chitin, chitosan and heparin.

40. The process of claim 25, wherein the first chemical substance is a chemical crosslinking agent.

41. The process of claim 40, wherein the chemical crosslinking agent is selected from the group consisting of glutaraldehyde, formaldehyde, divinyl sulfone, a carbodiimide, an epoxide and an imidazolo.

42. The process of claim 25, wherein the first chemical substance is an esterifying agent.

43. The process of claim 42, wherein the esterifying agent is selected from the group consisting of methanol, ethanol, propanol and butanol.

44. The process of claim 25, wherein the first chemical substance is an amidating agent.

45. The process of claim 44, wherein the amidating agent is selected from the group consisting of glutaric anhydride and succinic anhydride.

46. The process of claim 25, wherein the first chemical substance is an acylating agent.

47. The process of claim 46, wherein the acylating agent is selected from the group consisting of benzoylchloride and butyrylchloride.

48. The process of claim 29, wherein the collagen and the first synthetic hydrophilic polymer are covalently bound to each other by an ether linkage, and the collagen and the second synthetic hydrophilic polymer are covalently bound to each other by an ester linkage.

49. An implant coating comprising a collagen-synthetic polymer matrix prepared by a process comprising the steps of:

(a) covalently binding collagen with a first multifunctionally activated synthetic hydrophilic polymer to form a covalently binding collagen-synthetic polymer matrix intermediate;

(b) further reacting the covalently binding collagen-synthetic polymer matrix intermediate with a first chemical substance to form a modified covalently binding collagen-synthetic polymer matrix, wherein the chemical substance is selected from the group consisting of a second synthetic hydrophilic polymer, a chemical crosslinking agent, an esterifying agent, an amidating agent, an acylating agent, a functionally activated amino acid and a functionally activated peptide; and (c) binding a second chemical substance to the modified covalently binding collagen-synthetic polymer matrix, wherein the second chemical substance is selected from the group consisting of a biologically active agent, a glycosaminoglycan and a glycosaminoglycan derivative.

50. The implant coating of claim 49, wherein the second chemical substance is a biologically active agent.

51. The implant coating of claim 50, wherein the first chemical substance is a second synthetic hydrophilic polymer.

52. The implant coating of claim 49, wherein the first chemical substance is a second synthetic hydrophilic polymer.

53. The implant coating of claim 49, wherein the second chemical substance is a glycosaminoglycan or a glycosaminoglycan derivative.

54. The implant coating of any one of claims 49 to 53; wherein the coating is capable of being used to coat an implant selected from the group consisting of a vascular graft, a vascular stent and a vascular stent-graft combination.

55. A collagen-synthetic polymer matrix comprising:

(a) a multifunctionally activated synthetic hydrophilic polymer;

(b) covalently binding collagen covalently bound to the multifunctionally activated synthetic hydrophilic polymer; and (c) a biologically active agent covalently bound to the multifunctionally activated synthetic hydrophilic polymer;

wherein a majority of said biologically active agent is on a surface of the matrix.

* * * * *